US008877924B2

(12) United States Patent
Tao et al.

(10) Patent No.: US 8,877,924 B2
(45) Date of Patent: Nov. 4, 2014

(54) BENZYL SUBSTITUTED TRIAZINE DERIVATIVES AND THEIR THERAPEUTICAL APPLICATIONS

(75) Inventors: Chunlin Tao, Los Angeles, CA (US);
Qinwei Wang, Alhambra, CA (US);
David Ho, Monterey Park, CA (US);
Laxman Nallan, Alhambra, CA (US);
Tulay Polat, Los Angeles, CA (US);
Xiaowen Sun, Shanghai (CN); Neil Desai, Los Angeles, CA (US)

(73) Assignee: NantBio Inc., Culver City, CA (US)

( * ) Notice: Subject to any disclaimer, the term of this patent is extended or adjusted under 35 U.S.C. 154(b) by 31 days.

(21) Appl. No.: 13/377,031

(22) PCT Filed: Jun. 8, 2010

(86) PCT No.: PCT/US2010/037695
§ 371 (c)(1),
(2), (4) Date: Jul. 3, 2012

(87) PCT Pub. No.: WO2010/144394
PCT Pub. Date: Dec. 16, 2010

(65) Prior Publication Data
US 2012/0264759 A1 Oct. 18, 2012

Related U.S. Application Data

(60) Provisional application No. 61/185,419, filed on Jun. 9, 2009.

(51) Int. Cl.
C07D 403/04 (2006.01)
C07D 403/12 (2006.01)
C07D 403/14 (2006.01)
C07D 417/12 (2006.01)
C07D 417/14 (2006.01)
C07D 413/14 (2006.01)
C07D 409/14 (2006.01)
C07D 405/14 (2006.01)

(52) U.S. Cl.
CPC ............ C07D 403/12 (2013.01); C07D 417/12 (2013.01); C07D 417/14 (2013.01); C07D 413/14 (2013.01); C07D 409/14 (2013.01); C07D 405/14 (2013.01); C07D 403/14 (2013.01)
USPC ........................................................ 544/198

(58) Field of Classification Search
CPC ................................................... C07D 403/04
USPC ........................................................ 544/198
See application file for complete search history.

(56) References Cited

U.S. PATENT DOCUMENTS

| 5,451,596 | A  | 9/1995  | Ullrich et al. |
| 5,854,264 | A  | 12/1998 | Anthony et al. |
| 5,916,596 | A  | 6/1999  | Desai et al. |
| 6,340,683 | B1 | 1/2002  | Marzabadi et al. |
| 6,407,238 | B1 | 6/2002  | Baron et al. |
| 6,429,213 | B1 | 8/2002  | Xue et al. |
| 6,440,965 | B1 | 8/2002  | Kelley et al. |
| 6,498,165 | B1 | 12/2002 | Armstrong et al. |
| 6,506,405 | B1 | 1/2003  | Desai et al. |
| 6,537,579 | B1 | 3/2003  | Desai et al. |
| 6,596,746 | B1 | 7/2003  | Das et al. |
| 6,635,655 | B1 | 10/2003 | Jayyosi et al. |
| 6,653,332 | B2 | 11/2003 | Jaen et al. |
| 6,858,626 | B2 | 2/2005  | Xue et al. |
| 6,890,915 | B2 | 5/2005  | Sheppeck et al. |
| 6,906,053 | B2 | 6/2005  | Sheppeck et al. |
| 6,933,272 | B1 | 8/2005  | Helmerhorst et al. |
| 6,960,685 | B2 | 11/2005 | Watkins et al. |
| 7,005,440 | B1 | 2/2006  | Jayyosi et al. |
| 7,041,693 | B2 | 5/2006  | Sheppeck |
| 7,067,539 | B2 | 6/2006  | Kozlowski et al. |
| 7,151,118 | B2 | 12/2006 | Angell et al. |
| 7,157,487 | B2 | 1/2007  | Nakayama et al. |
| 7,211,671 | B2 | 5/2007  | Sheppeck et al. |
| 7,294,624 | B2 | 11/2007 | Duan et al. |
| 7,309,800 | B2 | 12/2007 | Angell et al. |
| 7,312,226 | B2 | 12/2007 | Hurley et al. |
| 7,326,712 | B2 | 2/2008  | Hurley et al. |
| 7,326,713 | B2 | 2/2008  | Hurley et al. |
| 7,335,662 | B2 | 2/2008  | Hurley et al. |
| 7,345,178 | B2 | 3/2008  | Nunes et al. |
| 7,396,843 | B2 | 7/2008  | Angell et al. |
| RE40,558  | E  | 10/2008 | Jayyosi et al. |
| 7,482,372 | B2 | 1/2009  | Sheppeck et al. |
| 7,507,767 | B2 | 3/2009  | Kozlowski et al. |
| 7,569,724 | B2 | 8/2009  | Watkins et al. |
| 7,585,846 | B2 | 9/2009  | Sheu et al. |
| 7,595,317 | B2 | 9/2009  | Duan et al. |
| 2002/0037928 | A1 | 3/2002 | Jaen et al. |
| 2003/0199516 | A1 | 10/2003 | Moser et al. |
| 2003/0220373 | A1 | 11/2003 | Jaye et al. |
| 2004/0087798 | A1 | 5/2004 | Yamada |
| 2004/0116388 | A1 | 6/2004 | Armistead et al. |

(Continued)

FOREIGN PATENT DOCUMENTS

CN 102119157 A 7/2011
JP 2003-511378 A 3/2003

(Continued)

OTHER PUBLICATIONS ptcl.chem.ox.ac.uk/MSDS.*
Kelarev et al., "Synthesis of amino derivatives of 1,3,5-triazine containing 1,3,4-thiadiazole fragments," *Izvestiya Vysshikh Uchebnykh Zavedenii, Khimiya i Khimicheskaya Tekhnologiya*, 1997, 40(5), 27-32, Chemical Abstracts Accession No. 1998:69514, CAS Registry No. 202462508, 1 p.
Nikolova et al., "SAR Applicability Domain," The European Commission, Joint Research Centre, Institute for Health & Consumer Protection, Sep. 27, 2004, 9 pp.

(Continued)

Primary Examiner — Shirley V Gembeh
(74) Attorney, Agent, or Firm — Leydig, Voit & Mayer, Ltd.

(57) ABSTRACT

The invention provides triazine compounds and methods of their use to modulate protein kinases and to treat diseases mediated by said protein kinases.

11 Claims, No Drawings

(56) References Cited

U.S. PATENT DOCUMENTS

| | | | |
|---|---|---|---|
| 2005/0065195 A1 | 3/2005 | Angell et al. | |
| 2005/0227983 A1 | 10/2005 | Timmer et al. | |
| 2005/0227992 A1 | 10/2005 | Hurley et al. | |
| 2005/0239794 A1 | 10/2005 | Hurley et al. | |
| 2005/0250945 A1 | 11/2005 | Li et al. | |
| 2005/0260126 A1 | 11/2005 | Kudo et al. | |
| 2005/0277658 A1 | 12/2005 | Hurley et al. | |
| 2006/0004010 A1 | 1/2006 | Habashita et al. | |
| 2006/0035897 A1 | 2/2006 | Caravatti et al. | |
| 2006/0035928 A1 | 2/2006 | Jaen et al. | |
| 2006/0122267 A1 | 6/2006 | Brookes et al. | |
| 2006/0160748 A1 | 7/2006 | Sheu et al. | |
| 2006/0293336 A1 | 12/2006 | Sutton et al. | |
| 2007/0049559 A1 | 3/2007 | Pfeffer et al. | |
| 2007/0099845 A1 | 5/2007 | Sheu et al. | |
| 2007/0185152 A1 | 8/2007 | Yamashita et al. | |
| 2007/0287707 A1 | 12/2007 | Arrington et al. | |
| 2007/0299067 A1 | 12/2007 | Liu et al. | |
| 2008/0051414 A1 | 2/2008 | Hurley et al. | |
| 2008/0096883 A1 | 4/2008 | Caravatti et al. | |
| 2008/0176853 A1* | 7/2008 | Tao et al. | 514/245 |
| 2008/0182847 A1 | 7/2008 | Augeri et al. | |
| 2009/0036419 A1 | 2/2009 | Chen et al. | |
| 2009/0099165 A1 | 4/2009 | Hurley et al. | |
| 2009/0099170 A1 | 4/2009 | Nunes et al. | |
| 2009/0099175 A1 | 4/2009 | Arrington et al. | |
| 2009/0137594 A1 | 5/2009 | Frank et al. | |
| 2009/0143399 A1 | 6/2009 | Hurley et al. | |
| 2009/0163476 A1 | 6/2009 | Milburn et al. | |

FOREIGN PATENT DOCUMENTS

| | | |
|---|---|---|
| JP | 2003-519143 A | 6/2003 |
| JP | 2004-516292 A | 3/2004 |
| JP | 2011-522870 A | 8/2011 |
| WO | 99/20275 A1 | 4/1999 |
| WO | 99/32106 A1 | 7/1999 |
| WO | WO 00/43369 A1 | 7/2000 |
| WO | 01/81311 A1 | 11/2001 |
| WO | 01/94341 A1 | 12/2001 |
| WO | 02/08205 A1 | 1/2002 |
| WO | 02/16352 A1 | 2/2002 |
| WO | WO 02/50066 A2 | 6/2002 |
| WO | 02/062750 A1 | 8/2002 |
| WO | 03/014111 A1 | 2/2003 |
| WO | 03/018021 A1 | 3/2003 |
| WO | 03/024448 A2 | 3/2003 |
| WO | 03/026666 A1 | 4/2003 |
| WO | WO 03/078426 A1 | 9/2003 |
| WO | 2004/058776 A1 | 7/2004 |
| WO | 2005/003103 A2 | 1/2005 |
| WO | 2005/007646 A1 | 1/2005 |
| WO | 2005/007648 A2 | 1/2005 |
| WO | 2005/011703 A1 | 2/2005 |
| WO | 2005/096784 A2 | 10/2005 |
| WO | 2005/118580 A2 | 12/2005 |
| WO | 2007/056016 A1 | 5/2007 |
| WO | 2008/026704 A1 | 3/2008 |
| WO | 2008/076883 A2 | 6/2008 |
| WO | 2008/116920 A2 | 10/2008 |
| WO | WO 2009/016410 A1 | 2/2009 |
| WO | WO 2009/091388 A2 | 7/2009 |
| WO | 2009/150462 A1 | 12/2009 |
| WO | WO 2009/150452 A1 | 12/2009 |

OTHER PUBLICATIONS

Parasharya et al., "s-Triazines. Part XI: 2-(5'-Benzoylaminomethyl-1',3',4'-thiadizol-2'-yl)amino-4-arylamino/(5'-anilino-1',3',4'-thiadiozol-2'-yl)thio/(benzthiazol-2'-yl)thio-6-arylamino-s-triazines," *J. of the Institution of Chemists*, 1991, 63(6), 196-8, Chemical Abstracts Accession No. 1992:571386, CAS Registry No. 143422326, 1 p.
Sharn et al., "Spatially Addressed Synthesis of Amino- and Amino-Oxy-Substituted 1,3,5-Triazine Arrays on Polymeric Membranes," *J. of Combinatorial Chem.*, 2000, 2(4), 361-369, Abstract XP002683813, Database Accession No. 2000:355907, Chemical Abstracts Service, Columbus, OH, 1 p.
Sharn et al., "Spatially Addressed Synthesis of Amino- and Amino-Oxy-Substituted 1,3,5-Triazine Arrays on Polymeric Membranes," *J. of Combinatorial Chem.*, 2000, 2(4), 361-369, Chemical Abstracts Accession No. 2000:355907, CAS Registry No. 286963437, 2 pp.
Australian Patent Office, Examination Report in Australian Patent Application No. 2010258964, Nov. 23, 2012, 12 ppl.
Canadian Intellectual Property Office, Office Action in Canadian Patent Application No. 2,765,044, Jan. 11, 2013, 3 pp.
Chinese State Intellectual Property Office, Office Action in Chinese Patent Application No. 201080034889.5, May 7, 2013, 24 pp.
European Patent Office, Extended European Search Report in European Patent Application No. 10786656.8, Oct. 2, 2012, 12 pp.
U.S. Patent Office, International Search Report in International Patent Application No. PCT/US2010/037695, Jul. 30, 2010, 2 pp.
U.S. Patent Office, Written Opinion in International Patent Application No. PCT/US2010/037695, Jul. 30, 2010, 4 pp.
Abram et al., *Experimental Cell Res.*, 254, 1-13 (2000).
Abu-Duhier et al., *Br. J. Haematology*, 113, 983-988 (2001).
Agnes et al., *Gene*, 145, 283-288 (1994).
Anand et al., *Cancer Cell*, 3, 51-62 (Jan. 2003).
Anderson et al., *Advances in Immunology*, 56, 151-178 (1994).
Appleby et al., *Cell*, 70, 751-763 (Sep. 4, 1992).
Bagley et al., *Org. Biomol. Chem.*, 4, 4158-4164 (2006).
Baindur et al., *J. Med. Chem.*, 48, 1717-1720 (2005).
Baliani et al., *J. Med. Chem.*, 48, 5570-5579 (2005).
Berdnik et al., *Current Biol.*, 12, 640-647 (Apr. 16, 2002).
Biscardi et al., *Advances in Cancer Research*, v. 76, 61-119 (1999).
Bolen, Joseph B., *Oncogene*, 8, 2025-2031 (1993).
Bolen et al., *Annu. Rev. Immunol.*, 15, 371-404 (1997).
Boschelli et al., *Drugs of the Future*, 25(7), 717-736 (2000).
Boschelli et al., *J. Med. Chem.*, 47, 1599-1601 (2004).
Boyce et al., *J. Clin. Invest.*, 90, 1622-1627 (Oct. 1992).
Brasel et al., *Leukemia*, 9, 1212-1218 (1995).
Brown et al., *Biochimica Biophysica Acta*, 1287, 121-149 (1996).
Brugge et al., *Nature*, 269, 346-348 (Sep. 22, 1977).
Cartwright et al., *Proc. Natl. Acad. Sci. USA*, 87, 558-562 (Jan. 1990).
Carvajal at al., *Clin. Cancer Res.*, 12, 6869-6875 (2006).
Collett et al., *Proc. Natl. Acad. Sci. USA*, 75(4), 2021-2024 (Apr. 1978).
Ditchfield et al., *J. Cell Biol.*, 161(2), 267-280 (Apr. 28, 2003).
Dosil et al., *Mol. Cell. Biol.*, 13(10), 6572-6585 (Oct. 1993).
Dutertre et al., *J. Cell Sci.*, 117, 2523-2531 (2004).
Egan et al., *Oncogene*, 18, 1227-1237 (1999).
Escribano et al., *Tetrahedron Lett.*, 29(46) 6001-6004 (1988).
Eyers et al., *Current Biol.*, 13, 691-697 (Apr. 15, 2003).
Fabbro et al., *Anti-Cancer Drug Design*, 15, 17-28 (2000).
Fancelli et al., *J. Med. Chem.*, 49, 7247-7251 (2006).
Fanning et al., *Cancer Research*, 52, 1457-1462 (Mar. 15, 1992).
Frame, Margaret C., *Biochim. Biophys. Acta*, 1602, 114-130 (2002).
Garcia-Bustos et al., *EMBO J.* 13(10), 2352-2361(1994).
Garnier et al., *J. Org. Chem.*, 69, 7809-7815 (2004).
Giet et al., *J. Cell Biol.*, 152(4), 669-681 (Feb. 19, 2001).
Giles et al., *Blood*, 102(3), 795-801 (Aug. 2003).
Goldman et al., *J. Clin. Invest.*, 102(2), 421-429 (Jul. 1998).
Goto et al., *J. Biol. Chem.*, 278(10), 8526-8530 (2003).
Griffin, James D., *Hematology J.*, 5, S188-S190 (2004).
Hamaguchi et al., *Oncogene*, 10, 1037-1043 (1995).
Hanks et al., *Faseb J.*, 9, 576-596 (1995).
Harrington et al., *Nature Med.*, 10(3), 262-267 (Mar. 2004).
Hata et al., *Cancer Res.*, 65, 2899-2905 (2005).
Hauf et al., *J. Cell Biol.*, 161(2), 281-294 (2003).
Hayakawa et al., *Oncogene*, 19, 624-631 (2000).
Hirota et al., *Cell*, 114, 585-598 (Sep. 5, 2003).
Hiwasa et al., *FEBS Lett.*, 444, 173-176 (1999).
Hoar et al., Clin. Cancer Res., 11 (24 Supp.), Abstract C40, p. 9109s (Dec. 15, 2005).
Horiike et al., *Leukemia*, 11, 1442-1446 (1997).

(56) References Cited

OTHER PUBLICATIONS

Hudlicky et al., *Reductions in Organic Chemistry*, 2$^{nd}$ ed., Chapter 2, pp. 19-30, "Reduction with Hydrides and Complex Hydrides," ACS Monograph 188, Washington D.C., American Chemical Society (1996).
Hunter et al., *Proc. Natl. Acad. Sci. USA*, 77(3), 1311-1315 (Mar. 1980).
Irby et al., *Nature Genetics*, 21, 187-190 (Feb. 1999).
Jankowski et al., *Gut*, 33, 1033-1038 (1992).
Kallio et al., *Current Biology*, 12, 900-905 (Jun. 4, 2002).
Kane et al., *Curr. Opn. Immunol.*, 12, 242-249 (2000).
Karni et al., *Oncogene*, 18, 4654-4662 (1999).
Kelly et al., *Cancer Cell*, 1, 421-432 (Jun. 2002).
Klein et al., *Mol. Cell. Biol.*, 17(11), 6427-6436 (Nov. 1997).
Klein et al., *EMBO J.*, 18(18), 5019-5027 (1999).
Knighton et al., *Science*, 253, 407-414 (Jul. 26, 1991).
Kufer et al., *J. Cell Biol.*, 158(4), 617-623 (Aug. 19, 2002).
Kumar et al., *J. Biol. Chem.*, 273(40), 25654-25658 (1998).
Kumar et al., *J. Med. Chem.*, 49(11), 3395-3401 (Jun. 2006).
Kunitoku et al., *Developmental Cell*, 5, 853-864 (Dec. 2003).
Lan et al., *Current Biology*, 14, 273-286 (Feb. 17, 2004).
Leftheris et al., *J. Med. Chem.*, 47, 6283-6291 (2004).
Lowell et al., *J. Leukocyte Biol.*, 65, 313-320 (Mar. 1999).
Lutz et al., *Biochem. Biophys. Res. Comm.*, 243, 503-508 (1998).
Lyman et al., *Cell*, 75, 1157-1167 (Dec. 17, 1993).
Lynch et al., *Leukemia*, 7(9), 1416-1422 (1993).
Mahadevan et al., *Expert Opn. Drug Discov.*, 2(7), 1011-1026 (2007).
Mao et al., *Oncogene*, 15, 3083-3090 (1997).
Maroc et al., *Oncogene*, 8, 909-918 (1993).
Marumoto et al., *J. Biol. Chem.*, 278(51), 51786-51795 (2003).
Mazurenko et al., *Eur. J. Cancer*, 28(2/3), 372-377 (1992).
Menicagli et al., *J. Med. Chem.*, 47, 4649-4652 (2004).
Meraldi et al, *EMBO J.*, 21(4), 483-492 (2002).
Mizuki et al., *Blood*, 96(12), 3907-3914 (Dec. 1, 2000).
Mizuki et al., *Blood*, 101(8), 3164-3173 (Apr. 15, 2003).
Moasser et al., *Cancer Research*, 59, 6145-6152 (Dec. 15, 1999).
Molina et al., *Nature*, 357, 161-164 (May 14, 1992).
Murata-Hori et al., *Current Biology*, 12, 894-899 (Jun. 4, 2002).
Muthuswamy et al., *Oncogene*, 11, 1801-1810 (1995).
Nakao et al., *Leukemia*, 10, 1911-1918 (1996).
O'Farrell et al., *Blood*, 101(9), 3597-3605 (May 2003).
Owens et al., *Mol. Biol. Cell*, 11, 51-64 (Jan. 2000).
Paul et al., *Nat. Med.*, 7(2), 222-227 (Feb. 2001).
Parang et al., *Curr. Opn. Drug Discovery & Development*, 7(5), 617-629 (2004).
Parang et al., *Expert Opin. Ther. Patents*, 15(9), 1183-1207 (2005).
Pawson, Tony, *Nature*, 373, 573-580 (Feb. 16, 1995).
Rodriguez et al., *J. Med. Chem.*, 47, 600-611 (2004).
Rosnet et al., *Genomics*, 9, 380-385 (1991).
Sakamoto et al., *Jpn. J. Cancer Res.*, 92, 941-946 (Sep. 2001).
Scheijen et al., *Oncogene*, 21, 3314-3333 (2002).
Schellens et al., *J. Clin. Oncol.*, 24(18S), Abstract 3008, p. 122S, (Jun. 20, 2006).
Schlessinger et al., *Neuron*, 9, 383-391 (Sep. 1992).
Severson et al., *Current Biology*, 10, 1162-1171 (2000).
Soriano et al., *Cell*, 64, 693-702 (Feb. 22, 1991).
Spiekermann et al., *Blood*, 101(4), 1494-1504 (Feb. 2003).
Staley et al., *Cell Growth & Differentiation*, 8, 269-274 (Mar. 1997).
Stanley et al., *J. Cell. Biochem.*, 21, 151-159 (1983).
Stirewalt et al., *Nature Reviews: Cancer*, 3, 650-665 (Sep. 2003).
Sun et al., *Biochemistry*, 44, 14455-14462 (2005).
Susa et al., *TiPS*, 21, 489-495 (Dec. 2000).
Takayanagi et al., *J. Clin. Invest.*, 104(2) 137-146 (Jul. 1999).
Talamonti et al., *J. Clin. Invest.*, 91, 53-60 (Jan. 1993).
Tatosyan et al., *Biochemistry (Moscow)*, 65(1), 49-58 (2000).
Taylor et al., *Mol. Cell. Biol.*, 15(8), 4149-4157 (Aug. 1995).
Thiede et al., *Blood*, 99(12), 4326-4335 (Jun. 15, 2002).
Thomas et al., *Annu. Rev. Cell Dev. Biol.*, 13, 513-609 (1997).
Turner et al., *Nature*, 402 (Supp), B24-B30 (Nov. 25, 1999).
Vicentini et al., *J. Immunol.*, 168, 6446-6454 (2002).
Warmuth et al., *Current Pharmaceutical Design*, 9, 2043-2059 (2003).
Weaver et al., *Cancer Cell*, 8, 7-12 (Jul. 2005).
Weisberg et al., *Cancer Cell*, 1, 433-443 (Jun. 2002).
Whitesell et al., *Current Cancer Drug Targets*, 3, 349-358 (2003).
Whitten et al., *J. Med. Chem.*, 39, 4354-4357 (1996).
Wiener et al., *Clin. Cancer Res.*, 5, 2164-2170 (Aug. 1999).
Yamamoto et al., *Blood*, 97(8), 2434-2439 (Apr. 15, 2001).
Yarden et al., *Nature*, 323, 226-232 (Sep. 18, 1986).
Yarden et al., *EMBO J.*, 6(11), 3341-3351 (1987).
Ye et al., *Biochemistry*, 43, 15775-15784 (2004).
Yeatman, Timothy J., *Nature Reviews: Cancer*, 4, 470-480 (Jun. 2004).
Yokota et al., *Leukemia*, 11, 1605-1609 (1997).
Zeitlin et al., *J. Cell. Biol.*, 155(7), 1147-1157 (Dec. 24, 2001).
Zhang et al., *Biochem. Biophys. Res. Comm.*, 254, 440-445 (1999).
Zheng et al., *Blood*, 103(1), 267-274 (Jan. 2004).
Japanese Patent Application No. 515033/2012, Office Action (Jul. 29, 2014).

\* cited by examiner

BENZYL SUBSTITUTED TRIAZINE DERIVATIVES AND THEIR THERAPEUTICAL APPLICATIONS

FIELD OF THE INVENTION

The present invention relates generally to the use of compounds to treat a variety of disorders, diseases and pathologic conditions and more specifically to the use of triazine compounds to modulate protein kinases and for treating protein kinase-mediated diseases.

BACKGROUND OF THE INVENTION

Protein kinases constitute a large family of structurally related enzymes that are responsible for the control of a variety of signal transduction processes within the cell. Protein kinases, containing a similar 250-300 amino acid catalytic domain, catalyze the phosphorylation of target protein substrates.

The kinases may be categorized into families by the substrates in the phosphorylate (e.g., protein-tyrosine, protein-serine/threonine, lipids, etc.). Tyrosine phosphorylation is a central event in the regulation of a variety of biological processes such as cell proliferation, migration, differentiation and survival. Several families of receptor and non-receptor tyrosine kinases control these events by catalyzing the transfer of phosphate from ATP to a tyrosine residue of specific cell protein targets. Sequence motifs have been identified that generally correspond to each of these kinase families [Hanks et al., FASEB J., (1995), 9, 576-596; Knighton et al., Science, (1991), 253, 407-414; Garcia-Bustos et al., EMBO J., (1994), 13:2352-2361). Examples of kinases in the protein kinase family include, without limitation, abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaft CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, Tie, Tie-2, TRK, Yes, and Zap70.

Studies indicated that protein kinases play a central role in the regulation and maintenance of a wide variety of cellular processes and cellular function. For example, kinase activity acts as molecular switches regulating cell proliferation, activation, and/or differentiation. Uncontrolled or excessive kinase activity has been observed in many disease states including benign and malignant proliferation disorders as well as diseases resulting from inappropriate activation of the immune system (autoimmune disorders), allograft rejection, and graft vs host disease.

It is reported that many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. In addition, endothelial cell specific receptor PTKs, such as VEGF-2 and Tie-2, mediate the angiogenic process and are involved in supporting the progression of cancers and other diseases involving uncontrolled vascularization. Accordingly, there has been a substantial effort in medicinal chemistry to find protein kinase inhibitors that are effective as therapeutic agents.

One kinase family of particular interest is the Src family of kinases. Src kinase is involved in proliferation and migration responses in many cell types, cell activation, adhesion, motility, and survival, growth factor receptor signaling, and osteoclast activation (Biscardi et al., *Adv. Cancer Res.* (1999), 76, 61-119; Yeatman et al., *Nat. Rev. Cancer* (2004), 4, 470-480; Owens, D. W.; McLean et al., *Mol. Biol. Cell* (2000), 11, 51-64). Members of the Src family include the following eight kinases in mammals: Src, Fyn, Yes, Fgr, Lyn, Hck, Lck, and Blk (Bolen et al., Annu. Rev. lmmunol, (1997), 15, 371). These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region (Brown et al., Biochim Biophys Acta (1996), 1287, 121-149; Tatosyan et al. *Biochemistry* (Moscow) 2000, 65, 49-58). SH4 domain contains the myristylation signals that guide the Src molecule to the cell membrane. This unique domain of Src proteins is responsible for their specific interaction with particular receptors and protein targets (Thomas et al., Annu Rev Cell Dev Biol (1997), 13, 513-609). The modulating regions, SH3 and SH2, control intra- as well as intermolecular interactions with protein substrates which affect Src catalytic activity, localization and association with protein targets (Pawson T., Nature (1995), 373, 573-580). The kinase domain, SH1, found in all proteins of the Src family, is responsible for the tyrosine kinase activity and has a central role in binding of substrates. The N-terminal half of Src kinase contains the site(s) for its tyrosine phosphorylation and regulates the catalytic activity of Src (Thomas et al., Annu Rev Cell Dev Biol (1997), 13: 513-609). v-Src differs from cellular Src (c-Src) on the basis of the structural differences in C-terminal region responsible for regulation of kinase activity.

The prototype member of the Src family protein tyrosine kinases was originally identified as the transforming protein (v-Src) of the oncogenic retrovirus, Rous sarcoma virus, RSV (Brugge et al., Nature (1977), 269, 346-348); Hamaguchi et al. (1995), Oncogene 10: 1037-1043). Viral v-Src is a mutated and activated version of a normal cellular protein (c-Src) with intrinsic tyrosine kinase activity (Collett et al., Proc Natl Acad Sci U S A (1978), 75, 2021-2024). This kinase phosphorylates its protein substrates exclusively on tyrosyl residues (Hunter et al., Proc Natl Acad Sci U S A (1980), 77, 1311-1315).

Investigations indicated that Src is a cytoplasmic protein tyrosine kinase, whose activation and recruitment to perimembranal signaling complexes has important implications for cellular fate. It has well-documented that Src protein levels and Src kinase activity are significantly elevated in human breast cancers (Muthuswamy et al., Oncogene, (1995), 11, 1801-1810); Wang et al., *Oncogene* (1999), 18, 1227-1237; Warmuth et al., *Curr. Pharm. Des.* (2003), 9, 2043-2059], colon cancers (Irby et al., *Nat Genet* (1999), 21, 187-190), pancreatic cancers (Lutz et al., *Biochem Biophys Res Commun* (1998), 243, 503-508], certain B-cell leukemias and lymphomas (Talamonti et al., *J. Clin. Invest.* (1993), 91, 53; Lutz et al., *Biochem. Biophys. Res.* (1998), 243, 503; Biscardi et al., *Adv. Cancer Res.* (1999), 76, 61; Lynch et al., *Leukemia* (1993), 7, 1416; Boschelli et al., *Drugs of the Future* (2000), 25(7), 717), gastrointestinal cancer (Cartwright et al., Proc. Natl. Acad. Sci. USA, (1990), 87, 558-562 and Mao et al., Oncogene, (1997), 15, 3083-3090), non-small cell lung cancers (NSCLCs) (Mazurenko et al., European Journal of Cancer, (1992), 28, 372-7), bladder cancer (Fanning et al., Cancer Research, (1992), 52, 1457-62), oesophageal cancer (Jankowski et al., Gut, (1992), 33, 1033-8), prostate and ovarian cancer (Wiener et al., Clin. Cancer Research, (1999), 5, 2164-70), melanoma and sarcoma (Bohlen et al., Oncogene, (1993), 8, 2025-2031; tatosyan et al., *Biochemistry* (Moscow) (2000), 65, 49-58). Furthermore, Src kinase modulates signal transduction through multiple oncogenic pathways, including EGFR, Her2/neu, PDGFR, FGFR, and VEGFR (Frame et al., *Biochim. Biophys. Acta* (2002), 1602, 114-130; Sakamoto et al., Jpn J Cancer Res, (2001), 92: 941-946).

Thus, it is anticipated that blocking signaling through the inhibition of the kinase activity of Src will be an effective means of modulating aberrant pathways that drive oncologic transformation of cells. Src kinase inhibitors may be useful anti-cancer agents (Abram et al., Exp. Cell Res., (2000), 254, 1). It is reported that inhibitors of src kinase had significant antiproliferative activity against cancer cell lines (M.M. Moasser et al., Cancer Res., (1999), 59, 6145; Tatosyan et al., *Biochemistry* (Moscow) (2000), 65, 49-58).) and inhibited the transformation of cells to an oncogenic phenotype (R. Karni et al., Oncogene (1999), 18, 4654). Furthermore, antisense Src expressed in ovarian and colon tumor cells has been shown to inhibit tumor growth (Wiener et al., *Clin. Cancer Res.*, (1999), 5, 2164; Staley et al., *Cell Growth Diff.* (1997), 8, 269). Src kinase inhibitors have also been reported to be effective in an animal model of cerebral ischemia (Paul et al. Nature Medicine, (2001), 7, 222), suggesting that Src kinase inhibitors may be effective at limiting brain damage following stroke. Suppression of arthritic bone destruction has been achieved by the overexpression of CSK in rheumatoid synoviocytes and osteoclasts (Takayanagi et al., *J. Clin. Invest.* (1999), 104, 137). CSK, or C-terminal Src kinase, phosphorylates and thereby inhibits Src catalytic activity. This implies that Src inhibition may prevent joint destruction that is characteristic in patients suffering from rheumatoid arthritis (Boschelli et al., *Drugs of the Future* (2000), 25(7), 717).

It is well documented that Src-family kinases are also important for signaling downstream of other immune cell receptors. Fyn, like Lck, is involved in TCR signaling in T cells (Appleby et al., Cell, (1992), 70, 751). Hck and Fgr are involved in Fcγ receptor signaling leading to neutrophil activation (Vicentini et al., J. Immunol. (2002), 168, 6446). Lyn and Src also participate in Fcγ receptor signaling leading to release of histamine and other allergic mediators (Turner, H. and Kinet, J-P Nature (1999), 402, B24). These-findings suggest that Src family kinase inhibitors may be useful in treating allergic diseases and asthma.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis (Molina et al., *Nature*, (1992), 357, 161).

Hck is a member of the Src protein-tyrosine kinase family and is expressed strongly in macrophages, an important HIV target cell and its inhibition in HIV-infected macrophages might slow disease progression (Ye et al., *Biochemistry*, (2004), 43 (50), 15775 -15784).

Hck, Fgr and Lyn have been identified as important mediators of integrin signaling in myeloid leukocytes (Lowell et al., *J. Leukoc. Biol.*, (1999), 65, 313). Inhibition of these kinase mediators may therefore be useful for treating inflammation (Boschelli et al., *Drugs of the Future* (2000), 25(7), 717).

It is reported that Syk is a tyrosine kinase that plays a critical role in the cell degranulation and eosinophil activation and Syk kinase is implicated in various allergic disorders, in particular asthma (Taylor et al., *Mol. Cell. Biol.* (1995), 15, 4149).

BCR-ABL encodes the BCR-AEL protein, a constitutively active cytoplasmic tyrosine kinase present in 90% of all patients with chronic myelogenous leukemia (CML) and in 15-30% of adult patients with acute lymphoblastic leukemia (ALL). Numerous studies have demonstrated that the activity of BCR-ABL is required for the cancer causing ability of this chimeric protein.

Src kinases play a role in the replication of hepatitis B virus. The virally encoded transcription factor HBx activates Src in a step required for propagation of the virus (Klein et al., *EMBO J.* (1999), 18, 5019; Klein et al., *Mol. Cell. Biol.* (1997), 17, 6427). Some genetic and biochemical data clearly demonstrate that Src-family tyrosine kinases serve as a critical signal relay, via phosphorylation of c-Cbl, for fat accumulation, and provide potential new strategies for treating obesity (Sun et al., *Biochemistry*, (2005), 44 (44), 14455 -14462). Since Src plays a role in additional signaling pathways, Src inhibitors are also being pursued for the treatment of other diseases including osteoporosis and stroke (Susva et al., *Trends Pharmacol. Sci.* (2000), 21, 489-495; Paul et al., *Nat. Med.* (2001), 7, 222-227).

It is also possible that inhibitors of the Src kinase activity are useful in the treatment of osteoporosis (Soriano et al., Cell (1991), 64, 693; Boyce et al. J Clin. Invest (1992), 90, 1622; Owens et al., *Mol. Biol. Cell* (2000), 11, 51-64), T cell mediated inflammation (Anderson et al., Adv. Immunol. (1994), 56, 151; Goldman, F D et al. J. Clin. Invest. (1998), 102, 421), and cerebral ischemia (Paul et al. Nature Medicine (2001), 7, 222).

In addition, src family kinases participate in signal transduction in several cell types. For example, fyn, like Ick, is involved in T-cell activation. Hck and fgr are involved in Fe gamma receptor mediated oxidative burst of neutrophils. Src and lyn are believed to be important in Fc epsilon induced degranulation of mast cells, and so may play a role in asthma and other allergic diseases. The kinase lyn is known to be involved in the cellular response to DNA damage induced by UV light (Hiwasa et al., FEBS Lett. (1999), 444, 173) or ionizing radiation (Kumar et al., J Biol Chein, (1998), 273, 25654). Inhibitors of lyn kinase may thus be useful as potentiators in radiation therapy.

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor, which is expressed on the cell surface. This activation triggers a series of intracellular signaling cascades mediated by enzymes expressed within the cell (Kane et al. Current Opinion in Immunol. (2000), 12, 242). These cascades lead to gene regulation events that result in the production of cytokines, like interleukin-2 (IL-2). IL-2 is a necessary cytokine in T cell activation, leading to proliferation and amplification of specific immune responses.

Therefore, Src kinase and other kinase have become intriguing targets for drug discovery (Parang et al., *Expert Opin. Ther. Pat.* (2005), 15, 1183-1207; Parang et al., *Curr. Opin. Drug Discovery Dev.* (2004), 7, 630-638). Many classes of compounds have been disclosed to modulate or, more specifically, inhibit kinase activity for use to treat kinase-related conditions or other disorders. For example, U.S. Pat. No. 6,596,746 and the PCT WO 05/096784A2 disclosed benzotrianes as inhibitors of kinases; the PCT WO 01/81311 disclosed substituted benzoic acid amides for the inhibition of angiogenisis; U.S. Pat. No. 6,440,965, disclosed substituted pyrimidine derivatives in the treatment of neurodegenerative or neurological disorders; PCT WO 02/08205 reported the pyrimidine derivatives having neurotrophic activity; PCT WO 03/014111 disclosed arylpiperazines and arylpiperidines and their use as metalloproteinase inhibiting agents; PCT WO 03/024448 described compounds as inhibitors of histone deacetylase enzymatic activity; PCT WO 04/058776 disclosed compounds which possess anti-angiogenic activity. PCT WO 01/94341 and WO 02/16352 disclosed Src kinase inhibitors of quinazoline derivatives. PCT WO03/026666A1and WO03/018021A1 disclosed pyrimidinyl derivatives as kinase inhibitors. U.S. Pat. No 6,498,165 reported Src kinase inhibitor compounds of pyrimidine compounds. Peptides as Src Tyrosine Kinase Inhibitors is reported recently (Kumar et al., *J. Med. Chem.*, (2006), 49 (11), 3395-3401). The quinolinecarbonitriles derivatives was reported to be potent dual Inhibitors of Src and Abl Kinases (Diane et al., *J. Med. Chem.*, (2004), 47 (7), 1599-1601). Another kinase family of particular interest is the aurora kinases. The Aurora kinase family is a collection of highly related serine/threonine kinase that are key regulators of mitosis, essential for accurate and equal segtion of genomic material from parent to daught cells. Members of the Aurora kinase family include three related kinases kown as Aurora-A, Aurora-B, and Aurora-C. Despite significant sequence homology, the localization and functions of these kinases are largely distinct from one another (Richard D. Carvajal, et al. Clin Cancer Res 2006;12(23): 6869-6875; Daruka Mahadevan, et al. Expert Opin. Drug Discov. 2007 2(7): 1011-1026) .

Aurora-A is ubiquitously expressed and regulates cell cycle events occurring from late S phase through M phase, including centrosome maturation (Berdnik D, et al. Curr Biol 2002; 12:640-7), mitotic entry (Hirota T, et al. Cell 2003;114:585-98; Dutertre S, et al. J Cell Sci 2004;117:2523-31), centrosome separation (Marumoto T, et al. J Biol Chem 2003; 278:51786-95), bipolar-spindle assembly (Kufer T A, et al. J Cell Biol 2002;158:617-23; Eyers P A, et al. Curr Biol 2003; 13:691-7.), chromosome alignment on the metaphase plate (Marumoto T, et al. J Biol Chem 2003;278:51786-95; Kunitoku N, et al. Dev Cell 2003;5:853-64.), cytokinesis (Marumoto T, et al. J Biol Chem 2003;278:51786-95), and mitotic exit. Aurora-A protein levels and kinase activity both increase from late G2 through M phase, with peak activity in prometaphase. Once activated, Aurora-A mediates its multiple functions by interacting with various substrates including centrosomin, transforming acidic coiled-coil protein, cdc25b, Eg5, and centromere protein A.

Aurora-B is a chromosomal passenger protein critical for accurate chromosomal segregation, cytokinesis (Hauf S, et al. J Cell Biol 2003;161:281-94; Ditchfield C, et al. J Cell Biol 2003;161:267-80; Giet R, et al. J Cell Biol 2001;152:669-82; Goto H, et al. J Biol Chem 2003;278:8526-30), protein localization to the centromere and kinetochore, correct microtubule-kinetochore attachments (Murata-Hori M, et al. Curr Biol 2002;12:894-9), and regulation of the mitotic checkpoint. Aurora-B localizes first to the chromosomes during prophase and then to the inner centromere region between sister chromatids during prometaphase and metaphase (Zeitlin S G, et al. J Cell Biol 2001;155:1147-57). Aurora-B participates in the establishment of chromosomal biorientation, a condition where sister kinetochores are linked to opposite poles of the bipolar spindle via amphitelic attachments. Errors in this process, manifesting as a merotelic attachment state (one kinetochore attached to microtubules from both poles) or a syntelic attachment state (both sister kinetochores attached to microtubules from the same pole), lead to chromosomal instability and aneuploidy if not corrected before the onset of anaphase. The primary role of Aurora-B at this point of mitosis is to repair incorrect microtubule-kinetochore attachments (Hauf S, et al. J Cell Biol 2003;161:281-94; Ditchfield C, et al. J Cell Biol 2003;161:267-80; Lan W, et al. Curr Biol 2004;14:273-86.). Without Aurora-B activity, the mitotic checkpoint is compromised, resulting in increased numbers of aneuploid cells, genetic instability, and tumorigenesis (Weaver B A, et al. Cancer Cell 2005;8:7-12).

Aurora-A overexpression is a necessary feature of Aurora-A-induced tumorigenesis. In cells with Aurora-A overexpression, mitosis is characterized by the presence of multiple centrosomes and multipolar spindles (Meraldi P et al. EMBO J 2002;21:483-92.). Despite the resulting aberrant microtubule-kinetochore attachments, cells abrogate the mitotic checkpoint and progress from metaphase to anaphase, resulting in numerous chromosomal separation defects. These cells fail to undergo cytokinesis, and, with additional cell cycles, polyploidy and progressive chromosomal instability develop (Anand S, et al. Cancer Cell 2003;3:51-62).

The evidence linking Aurora overexpression and malignancy has stimulated interest in developing Aurora inhibitors for cancer therapy. In normal cells, Aurora-A inhibition results in delayed, but not blocked, mitotic entry, centrosome separation defects resulting in unipolar mitotic spindles, and failure of cytokinesis (Marumoto T, et al. J Biol Chem 2003;278: 51786-95). Encouraging antitumor effects with Aurora-A inhibition were shown in three human pancreatic cancer cell lines (Panc-1, MIA PaCa-2, and SU.86.86), with growth suppression in cell culture and near-total abrogation of tumorigenicity in mouse xenografts (Hata T, et al. Cancer Res 2005; 65:2899-905.).

Aurora-B inhibition results in abnormal kinetochore-microtubule attachments, failure to achieve chromosomal biorientation, and failure of cytokinesis (Goto H, et al. J Biol Chem 2003;278:8526-30; Severson AF, et al. Curr Biol 2000;10: 1162-71). Recurrent cycles of aberrant mitosis without cytokinesis result in massive polyploidy and, ultimately, to apoptosis (Hauf S, et al. J Cell Biol 2003;161:281-94; Ditchfield C, et al. J Cell Biol 2003;161:267-80; Giet R, et al. J Cell Biol 2001;152:669-82; Murata-Hori M, Curr Biol 2002;12: 894-9; Kallio M J, et al. Curr Biol 2002;12:900-5).

Inhibition of Aurora-A or Aurora-B activity in tumor cells results in impaired chromosome alignment, abrogation of the mitotic checkpoint, polyploidy, and subsequent cell death. These in vitro effects are greater in transformed cells than in either non-transformed or non-dividing cells (Ditchfield C, et al. J Cell Biol 2003;161:267-80). Thus, targeting Aurora may achieve in vivo selectivity for cancer. Although toxicity to rapidly dividing cell of the hematopoietic and gastrointestinal system is expected, the activity and clinical tolerability shown in xenograft models indicates the presence of a reasonable therapeutic index. Given the preclinical antitumor activity and potential for tumor selectivity, several Aurora kinase inhibitors have been developed. The first three small-molecule inhibitors of Aurora described include ZM447439 (Ditchfield C, et al. J Cell Biol 2003;161:267-80), Hesperadin (Hauf S, et al. J Cell Biol 2003;161:281-94), and MK0457 (VX680) (Harrington E A, et al. Nat Med 2004;10:262-7). The following agents are nonspecific inhibitors: ZM447439 inhibits Aurora-A and Aurora-B; Herperadin inhibits primarily Aurora-B; MK0457 inhibits all three Aurora kinases. Each induces a similar phenotype in cell-based assays, characterized by inhibition of phosphorylation of histone H3 on Ser10, inhibition of cytokinesis, and the development of polyploidy. Selective inhibitors of Aurora have also been developed. A selective Aurora-A inhibitor is MLN8054 (Hoar HM, et al. [abstract C40]. Proc AACR-NCI-EORTC International Conference: Molecular Targets and Cancer Therapeutics 2005). A expmple of selective Aurora-B inhibitor is AZD1152 (Schellens J, et al. [abstract 3008]. Proc Am Soc Clin Oncol 2006;24:122s). The next generation of Aurora inhibitors is currently being developed, including agents by Nerviano Medical Sciences (PHA-680632 and PHA-739358), Rigel (R763), Sunesis (SNS-314), NCE Discovery Ltd. (NCED#17), Astex Therapeutics (AT9283), and Montigen Pharmaceuticals (MP-235 and MP-529). Several of these agents are undergoing evaluation in clinical trials.

Many cancers are characterized by distruptions in cellular signaling pathways that lead to uncontrolled growth and proliferation of cancerous cells. Receptor tyrosine kinases (RTKs) play a crucial role in these signaling pathways, transmitting extracellular molecular signals into cytoplasm and/or nucleus of a cell. RTKs are transmembrane proteins that generally include an extracellular ligand-binding domain, a membrane-spanning domain and a catalytic cytoplasmic tyrosine kinase domain. The binding of ligand to the extracellular potion is believed to promote dimerization, resulting in trans-phosphorylation and activation of the intracellular tyrosine kinase domain (Schlessinger et al. Neuron 1992;9: 383-391).

Another kinase family of particular interest is FLT3. FMS-related tyrosine kinase 3 (FLT3), also known as FLK-2 (fetal liver kinase 2) and STK-1 (human stem cell kinase 1), belongs to a member of the class III receptor tyrosine kinase (RTKIII) family that include KIT, PDGFR, FMS and FLT1 (Stirewalt D L, et al. Nat. Rev. Cancer 2003;3:650-665; Rosnet O, et al. Genomics 1991;9:380-385; Yarden Y, et al. Nature 1986;323: 226-232; Stanley E R, et. al. J. Cell. Biochem.1983 21:151-159; Yarden Y, et al. EMBO J 1987;6:3341-3351). FLT3 is a membrane-spanning protein and composed of four domains; an extracellular ligand-binding domains consisting of five immunoglobin-like structures, a transmembrane (TM) domain, a juxtamembrane (JM) domain and a cytoplasmic C-Terminal tyrosine kinase (TK) domain. (Agnes F, et al. Gene 1994;145:283-288; Scheijen B, et al. Oncogene 2002; 21:3314-3333).

The ligand for FLT3 (FLT3 or FL) was cloned in 1993 and shown to be a Type I transmembrane protein expressed in cells of the hematopoietic bone marrow microenvironment, including bone marrow fibroblasts and other cells (Lyman S D, et al. Cell 1993;75:1157-1167). Both the membrane-bound and soluable forms can activate the tyrosine kinase activity of the receptor and stimulate growth of progenitor cells in the marrow and blood. Binding of ligand to receptor induces dimerisation of the receptor and activation of the kinase domains; which then autophosphorylate and catalyse phosphorylation of substrate proteins of various signal transduction pathways such as signal transducer and activator of transcription 5 (STAT5), RAS/mitogen-activated protein kinase (RAS/MAPK), phosphoinositide 3-kinase (Pl3K), src homologous and collagen gene (SHC), SH2-containing inositol-5-phosphatase (SHIP), and cytoplasmic tyrosine phosphatase with 2 Src-homology 2 (SH2) domains (SHP2), which play important roles in cellular proliferation, differentiation, and survival (Dosil M, et al. Mol Cell Biol 1993;13: 6572-6585. Zhang S, Biochem Biophys Res Commun 1999; 254:440-445). In addition to hemotopoietic cells, FLT3 gene is also expressed in placenta, gonads and brain (Maroc N, et al. Oncogene 1993;8:909-918) and also plays an important role in the immune response (deLapeyriere O, et al. Leukemia 1995;9:1212-1218).

FLT3 is overexpressed at the levels in 70-100% of cases of acute myeloid leukemias (AML), and in a high percentage of T-acute lymphocytic leukemia (ALL) cases (Griffin JD, et al. Haematol J. 2004;5:188-190). It is also overexpressed in a smaller subset of chronic myeloid leukemia (CML) in blast crisis. Studies have shown that the leukemic cells of B lineage ALL and AML frequently co-express FL, setting up autocrine or paracrine signaling loops that result in the constitutive activation of FLT3 (Zheng R, et. al. Blood. 2004;103:267-274).

Evidence is rapidly accumulating that many types of leukemias and myeloproliferative syndromes have mutation in tyrosine kinases. FLT3 mutations are one of the most frequent somatic alterations in AML, occurring in approximately ⅓ of patients. There are two types of activating mutations in FLT3 described in patients with leukemia. These include a spectrum of internal tandem duplications (ITD) occurring within the auto-inhibitory juxtamembrane s domain (Nakao M, et al. Leukemia 1996;10:1911-1918; Thiede C, et al. Blood 2002; 99:4326-4335), and activation loop mutations that include Asp835Tyr (D835Y), Asp835Val (D835V), Asp835His (D835H), Asp835Glu (D835E), Asp835Ala (D835A), Asp835Asn (D835N), Asp835 deletion and lle836 deletion (Yamamoto Y, et al., Blood 2001:97:2434-2439; Abu-Duhier F M, et al. Br. J. Haematol. 2001;113:983-988). Internal tandem duplication (ITD) mutations within the JM domain contribute to about 17-34% of FLT3 activating mutations in AML. FLT3-ITD has also been detected at low frequency in myelodysplastic syndrome (MDS) (Yokota S, et al. Leukemia 1997;11:1605-1609; Horiike S, et al. Leukemia 1997;11: 1442-1446). The ITDs are always in-frame, and are limited to the JM domain. However, they vary in length and position from patient to patient. These repeat sequences may serve to disrupt the autoinhibitory activity of the JM domain resulting in the constitutive activation of FLT3. Both FLT3-ITD and FLT3-Asp835 mutations are associated with FLT3 autophosphorylation and phosphorylation of downstream targets (Mizuki M, et al. Blood 2000;96:3907-3914; Mizuki M, et al. Blood 2003;101:3164-3173; Hayakawa F, et al. Oncogene 2000;19: 624-631).

Inhibitors of FLT3 are presently being studied and have reached clinical trials as monotherapy in relapsed or refractory AML patients, some or all of whom had FLT3 mutations. FLT3 inhibitors, such as PKC412 (N-benzoyl staurosporine) (Fabbro D, et al. Anticancer Drug Des 2000;15:17-28; Weisberg E, et al. Cancer Cell 2002;1:433-443), CT53518 (also known as MLN518) (Kelly LM, et al. Cancer Cell 2002;1: 421-432), SU11248 (O'Farrell A M, et al. Blood 2003;101: 3597-3605), SU5614 (Spiekermann K, et al. Blood 2003; 101:1494-1504), and SU5416 (Giles F J, et al. Blood 2003; 102:795-801), have been shown to have antitumor activity. Collectively, these data suggest that FLT3 is an attractive therapeutic target for the development of kinase inhibitors for AML and other associated diseases.

Considering the lack of currently available treatment options for the majority of the conditions associated with protein kinases, there is still a great need for new therapeutic agents that inhibit these protein targets. Particularly, Aurora kinase inhibors are of special intrest in treating certain disorders, including cancer.

SUMMARY OF THE INVENTION

Accordingly, it is an objective of the present invention to provide an antitumor agent comprising a triazine derivative as described in formula (I), pharmaceutically-acceptable formulations thereof, methods for making novel compounds and compositions for using the compounds. The compounds and compositions comprising the compounds in formula (I) have utility in treatment of a variety of diseases.

The combination therapy described herein may be provided by the preparation of the triazine derivative of formula (I) and the other therapeutic agent as separate pharmaceutical formulations followed by the administration thereof to a patient simultaneously, semi-simultaneously, separately or over regular intervals.

The present invention provides methods of use for certain chemical compounds such as kinase inhibitors for treatment of various diseases, disorders, and pathologies, for example, cancer, and vascular disorders, such as myocardial infarction (MI), stroke, or ischemia. The triazine compounds described in this invention may block the enzymatic activity of some or many of the members of the Aurora kinase family, in addition to blocking the activity of other receptor and non-receptor kinase. Such compounds may be beneficial for treatment of the diseases where disorders affect cell motility, adhesion, and cell cycle progression, and in addition, diseases with related hypoxic conditions, osteoporosis and conditions, which result from or are related to increases in vascular permeability, inflammation or respiratory distress, tumor growth, invasion, angiogenesis, metastases and apoptosis.

DETAILED DESCRIPTION OF THE INVENTION

The present invention is related to compounds showed as in Formula (I)

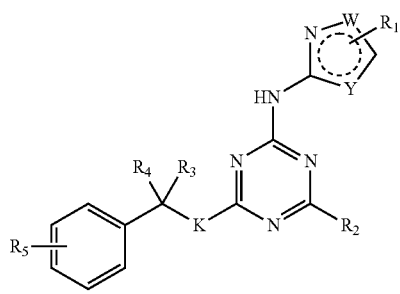

or a pharmaceutically acceptable salt thereof, wherein:

W and Y are independently selected from S, O, NR6, or CR6

R6 is independently selected from hydrogen or an optionally substituted C1-4 aliphatic group.

K is selected from —NR6, O, or S

R1 represents hydrogen, halogen, hydroxy, amino, cyano, alkyl, cycloalkyl, alkenyl, alkynyl, alkylthio, aryl, arylalkyl, heterocyclic, heteroaryl, heterocycloalkyl, alkylsulfonyl, alkoxycarbonyl and alkylcarbonyl.

R2 is selected from:

(i) $C_1$-$C_6$ alkyl, $C_2$-$C_6$ alkenyl, $C_2$-$C_6$ alkynyl, $C_3$-$C_{10}$ aryl or heteroaryl, $(C_3$-$C_7$cycloalkyl)$C_1$-$C_4$alkyl, $C_1$-$C_6$ haloalkyl, each of which is substituted with from 0 to 4 substituents independently chosen from halogen, hydroxy, cyano, amino, —COOH and oxo;

(ii) amino, alkyl amino, aryl amino, heteroaryl amino;

(iii) groups of the formula (Ia):

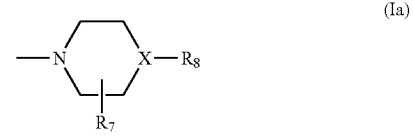

wherein:
$R_7$ represents hydrogen, $C_1$-$C_4$ alkyl, oxo;
X is CH, when $R_8$ is hydrogen; or X-$R_8$ is O; or X is N, $R_8$ represents groups of hydrogen, $C_1$-$C_6$ alkyl, $C_2$-$C_6$ alkenyl, $C_2$-$C_6$alkynyl, $C_3$-$C_{10}$ aryl or heteroaryl, $(C_3$-$C_7$cycloalkyl)$C_1$-$C_4$alkyl, $C_1$-$C_6$ haloalkyl, $C_1$-$C_6$alkoxy, $C_1$-$C_6$ alkylthio, $C_2$-$C_6$alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$alkylsulfonyl, mono- and di-($C_1$-$C_6$ alkyl) sulfonamido, and mono- and di-($C_1$-$C_6$alkyl)aminocarbonyl, each of which is substituted with from 0 to 4 substituents independently chosen from halogen, hydroxy, cyano, amino, —COOH and oxo;

R3 and R4 are independently selected from: Hydrogene, $C_1$-$C_6$ alkyl, $C_2$-$C_6$alkenyl, $C_2$-$C_6$alkynyl, $C_3$-$C_{10}$ aryl or heteroaryl, $(C_3$-$C_7$cycloalkyl)$C_1$-$C_4$alkyl, $C_1$-$C_6$ haloalkyl, hydroxy, cyano, amino, —COOH and oxo;

R5 is 0 to 5 substituents independently chosen from:

(i) halogen, hydroxy, amino, amide, cyano, —COOH, —SO$_2$NH$_2$, oxo, nitro and alkoxycarbonyl; and (ii) $C_1$-$C_6$ alkyl, $C_1$-$C_6$alkoxy, $C_3$-$C_{10}$ cycloalkyl, $C_2$-$C_6$ alkenyl, $C_2$-$C_6$alkynyl, $C_2$-$C_6$ alkanoyl, $C_1$-$C_6$ haloalkyl, $C_1$-$C_6$haloalkoxy, mono- and di- ($C_1$-$C_6$alkyl)amino, $C_1$-$C_6$alkylsulfonyl, mono- and di-($C_1$-$C_6$alkyl) sulfonamido and mono- and di-($C_1$-$C_6$alkyl)aminocarbonyl; phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, oxo, imino, $C_1$-$C_4$alkyl, $C_1$-$C_4$alkoxy and $C_1$-$C_4$haloalkyl.

The present invention also relates to compounds as shown in Formula (A):

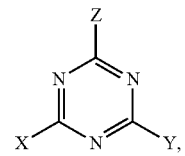

or a pharmaceutically acceptable salt thereof, wherein:
Y is selected from $C_1$-$C_6$ alkyl, $C_2$-$C_6$ alkenyl, $C_2$-$C_6$ alkynyl, —NR$^4$R$^5$, and -Q-R$^3$;
Q is heterocycloalkyl, which is optionally substituted with $C_1$-$C_4$ alkyl or oxo;
$R^3$ is selected from H, $C_1$-$C_6$ alkyl, $C_2$-$C_6$ alkenyl, $C_2$-$C_6$ alkynyl, aryl, and heteroaryl;
$R^4$ and $R^5$ are each independently selected from H, and $C_1$-$C_6$ alkyl;
X is —K—C(R$^4$)(R$^5$)-Ar$^1$-R$^1$;
K is selected from NR$^4$, S, and O;
Ar$^1$ is selected from aryl and heteroaryl, each of which is optionally substituted with halo, hydroxy, $C_1$-$C_6$ alkyl, $C_1$-$C_6$ haloalkyl, and $C_1$-$C_6$ alkoxy;
$R^1$ is one or more substituents independently selected from H, halo, —OR$^4$, $C_1$-$C_6$ alkyl, and $C_1$-$C_6$ haloalkyl;
Z is —NH-Ar$^2$-R$^2$;

Ar² is heteroaryl including at least one nitrogen, which heteroaryl is optionally substituted with halo, hydroxy, $C_1$-$C_6$ alkyl, $C_1$-$C_6$ haloalkyl, and $C_1$-$C_6$ alkoxy;

R² is one or more substituents independently selected from halo, hydroxy, $C_1$-$C_6$ alkyl, aryl, heteroaryl, $C_2$-$C_6$ alkenyl, and $C_2$-$C_6$ alkynyl, each of which is optionally substituted with halo, hydroxy, $C_1$-$C_6$ alkyl, $C_1$-$C_6$ haloalkyl, and $C_1$-$C_6$ alkoxy.

The present invention also relates to compounds as shown in Formula (A):

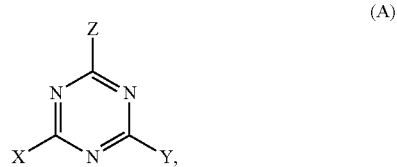

(A)

or a pharmaceutically acceptable salt thereof, wherein:

Y is -Q-R³;
Q is piperazinyl;
R³ is $C_1$-$C_6$ alkyl;
R⁴ and R⁵ are each independently selected from H, and $C_1$-$C_6$ alkyl;
X is —K—C(R⁴)(R⁵)-Ar¹-R¹;
K is selected from NR⁴, S, and O;
Ar¹ is selected from phenyl, and benzo[d][1,3]dioxolyl;
R¹ is selected from H, halo, —OR⁴, and $C^1$-$C_6$ alkyl;
Z is —NH-Ar²-R²;
Ar² is selected from thizaolyl and pyrazolyl;
R² is one or more substituents independently selected from halo, hydroxy, $C_1$-$C_6$ alkyl, phenyl, furanyl, $C_2$-$C_6$ alkenyl, and $C_2$-$C_6$ alkynyl.

The following definitions refer to the various terms used above and throughout the disclosure.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that include, variables (e.g. X, Ar.). Unless otherwise specified, each variable within such a formula is defined independently of any other variable, and any variable that occurs more than one time in a formula is defined independently at each occurrence.

The term "halo" or "halogen" refers to fluorine, chlorine, bromine or iodine.

The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—NH2), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine, The term 'cycloalkyl" herein alone or as part of another group refers to fully saturated and partially unsaturated hydrocarbon rings of 3 to 9, preferably 3 to 7 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —CO2H, —C(=O)H, CO2-alkyl, —C(=O)alkyl, keto, =N—OH, =N—O-alkyl, aryl, heteroaryl, heterocyclo, —NR'R", —C(=O)NR'R", —CO2NR'R", —C(=O)NR'R", —NR'CO2R", —NR'C(=O)R", —SO2NR'R", and —NR'SO2R", wherein each of R' and R" are independently selected from hydrogen, alkyl, substituted alkyl, and cycloalkyl, or R' and R" together form a heterocyclo or heteroaryl ring.

The term 'alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and like. Alkenyl groups may also be substituted at any available point of attachment. Exemplary substituents for alkenyl groups include those listed above for alkyl groups, and especially include C3 to C7 cycloalkyl groups such as cyclopropyl, cyclopentyl and cyclohexyl, which may be further substituted with, for example, amino, oxo, hydroxyl, etc.

The term "alkynyl" refers to straight or branched chain alkyne groups, which have one or more unsaturated carbon-carbon bonds, at least one of which is a triple bond. Alkynyl groups include C2-C8 alkynyl, C2-C6 alkynyl and C2-C4 alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Preferred alkoxy and alkylthio groups are those in which an alkyl group is attached via the heteroatom bridge. Preferred alkylthio groups have from 1 to 8 carbon atoms. Examples of such groups include the methylthio, ethylthio, n-propythiol, n-butylthiol, and like.

The term "oxo," as used herein, refers to a keto (C=O) group. An oxo group that is a substituent of a nonaromatic carbon atom results in a conversion of —CH2- to —C(=O)—.

The term "alkoxycarbonyl" herein alone or as part of another group denotes an alkoxy group bonded through a carbonyl group. An alkoxycarbonyl radical is represented by the formula: —C(O)OR, where the R group is a straight or branched C1-C6 alkyl group, cycloalkyl, aryl, or heteroaryl.

The term "alkylcarbonyl" herein alone or as part of another group refers to an alkyl group bonded through a carbonyl group or —C(O)R.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl S(O)m (m=0, 1, 2), or thiol.

The term "aromatic" refers to a cyclically conjugated molecular entity with a stability, due to delocalization, significantly greater than that of a hypothetical localized structure, such as the Kekule structure.

The term "amino" herein alone or as part of another group refers to —NH2. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "alkylsulfonyl" refers to groups of the formula (SO2)-alkyl, in which the sulfur atom is the point of attachment. Preferably, alkylsulfonyl groups include $C_1$-C6 alkylsulfonyl groups, which have from 1 to 6 carbon atoms. Methylsulfonyl is one representative alkylsulfonyl group.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom.

The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —CO2H, —C(=O)H, —CO2-alkyl, —C(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —CO2NR'R", —C(=O)NR'R", —NR'CO2R", —NR'C(=O)R", —SO2NR'R", and —NR'SO2R", wherein each of R' and R" is independently selected from hydrogen, alkyl, substituted alkyl, and cycloalkyl, or R' and R" together form a heterocyclo or heteroaryl ring.

Preferably monocyclic heteroaryl groups include pyrrolyl, pyrazolyl, pyrazolinyl, imidazolyl, oxazolyl, diazolyl, isoxazolyl, thiazolyl, thiadiazolyl, S isothiazolyl, furanyl, thienyl, oxadiazolyl, pyridyl, pyrazinyl, pyrimidinyl, pyridazinyl, triazinyl and the like. Preferably bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, dihydroisoindolyl, tetrahydroquinolinyl and the like.

Preferably tricyclic heteroaryl groups include carbazolyl, benzidolyl, phenanthrollinyl, acridinyl, phenanthridinyl, xanthenyl and the like.

The term "heterocycle" or "heterocycloalkyl" herein alone or as part of another group refers to a cycloalkyl group (non-aromatic) in which one of the carbon atoms in the ring is replaced by a heteroatom selected from O, S or N. The "heterocycle" has from 1 to 3 fused, pendant or Spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur.

Examples of "heterocycle" or "heterocycloalkyl groups include piperazine, piperidine, morpholine, thiomorpholine, pyrrolidine, imidazolidine and thiazolide.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member.

The term "optionally substituted " as it refers that the aryl or heterocyclyl or other group may be substituted at one or more substitutable positions by one or more groups independently selected from alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

A dash ("-") that is not between two letters or symbols is used to indicate a point of t attachment for a substituent. For example, —CONH2 is attached through the carbon atom.

A dashed cycle that locates inside of a heterocyle ring is used to indicate a conjugated system. The bonds between two atoms may be single bond or double bond.

The term "anticancer" agent includes any known agent that is useful for the treatment of cancer including, but is not limited, Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

The term "kinase" refers to any enzyme that catalyzes the addition of phosphate groups to a protein residue; for example, serine and threonine kineses catalyze the addition of phosphate groups to serine and threonine residues.

The terms "Src kinase," "Src kinase family," and "Src family" refer to the related homologs or analogs belonging to the mammalian family of Src kineses, including, for example, c-Src, Fyn, Yes and Lyn kineses and the hematopoietic-restricted kineses Hck, Fgr, Lck and Blk.

The term "therapeutically effective amount" refers to the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term 'pharmaceutically acceptable" refers to the fact that the carrier, diluent or excipient must be compatible with the other ingredients of the formulation and not deleterious to the recipient thereof.

The terms "administration of a compound" or "administering a compound" refer to the act of providing a compound of the invention or pharmaceutical composition to the subject in need of treatment.

The term "protected" refers that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., Protective Groups in Organic Synthesis, John Wiley & Sons, New York (1999).

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, s sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred. It will be apparent that each compound of Formula I may, but need not, be formulated as a hydrate, solvate or non-covalent complex. In addition, the various crystal forms and polymorphs are within the scope of the present invention. Also provided herein are prodrugs of the compounds of Formula I.

The term of "prodrug" refers a compound that may not fully satisfy the structural requirements of the compounds provided herein, but is modified in vivo, following administration to a patient, to produce a compound of Formula I, or other formula provided herein. For example, a prodrug may be an acylated derivative of a compound as provided herein. Prodrugs include compounds wherein hydroxy, amine or thiol groups are bonded to any group that, when administered to a mammalian subject, cleaves to form a free hydroxy, amino, or thiol group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

Groups that are "optionally substituted" are unsubstituted or are substituted by other than hydrogen at one or more available positions. Such optional substituents include, for example, hydroxy, halogen, cyano, nitro, C1-C6 alkyl, C2-C6 alkenyl, C2-C6 alkynyl, C1-C6 alkoxy, C2-C6 alkyl ether, C3-C6 alkanone, C2-C6 alkylthio, amino, mono- or di-(C1-C6 alkyl)amino, C1-C6 haloalkyl, —COOH, —CONH2, mono- or di-(C1-C6 alkyl)aminocarbonyl, —SO2NH2, and/or mono or di(C1-C6 alkyl) sulfonamido, as well as carbocyclic and heterocyclic groups.

Optional substitution is also indicated by the phrase "substituted with from 0 to X substituents," where X is the maximum number of possible substituents.

Certain optionally substituted groups are substituted with from 0 to 2, 3 or 4 independently selected substituents.

Preferred R1 groups of formula I are listed below:

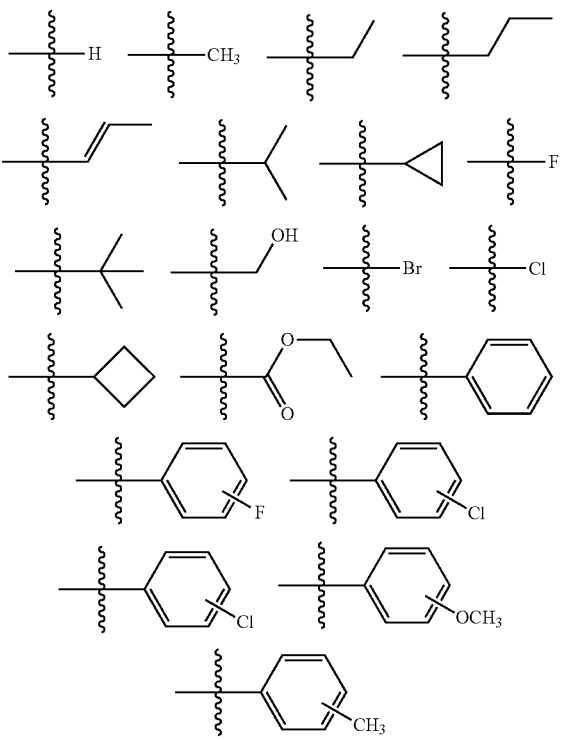

Preferred R2 groups of formula (I) are listed below:

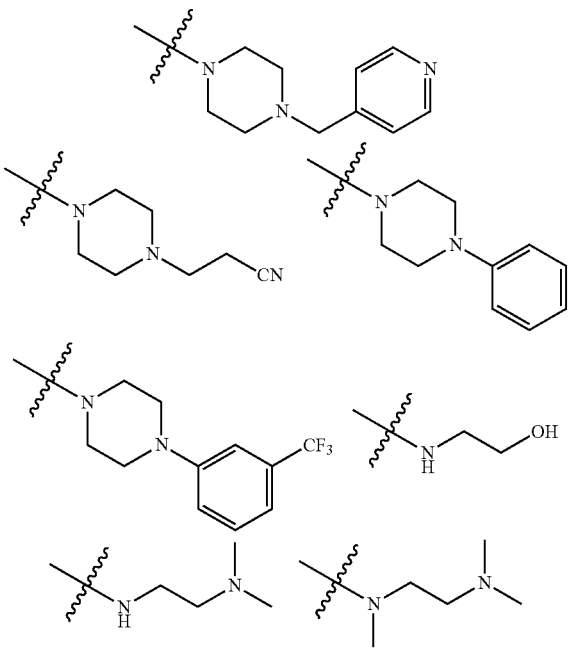

-continued

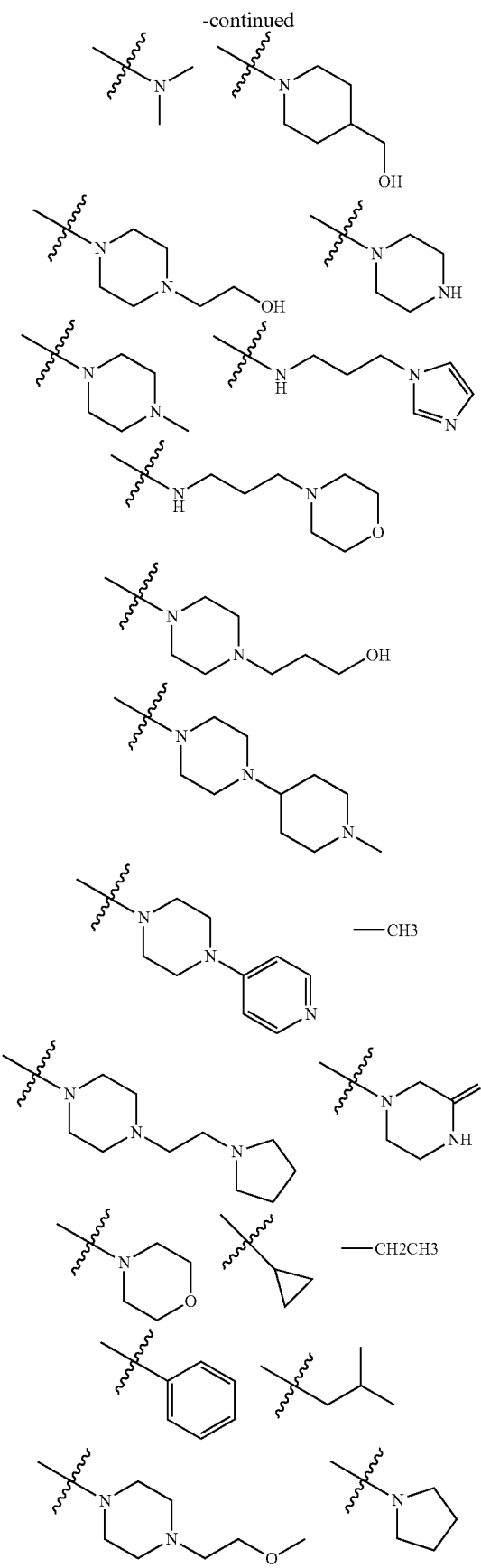

Preferred R3 and R4 groups of formula (I) are list below:
—H, —CH$_3$, —CH$_2$CH$_3$, —CH=CHCH$_3$, —CH$_2$CH$_2$CH$_3$, —CH$_2$CH$_2$CH$_2$CH$_3$, iso-propyl, cyclopropyl, cyclobutyl, tert-butyl, phenyl (-Ph), —CH$_2$OH, —CH$_2$CON(CH$_3$)$_2$, CH$_2$CONHCH$_3$, —COOCH$_2$CH$_3$, —Cl, —F, —Br.

Preferred R5 groups of formula (I) are list below, wherein the substitute may be the specific ones as defined here or may be one or multiple substitutes as defined above:

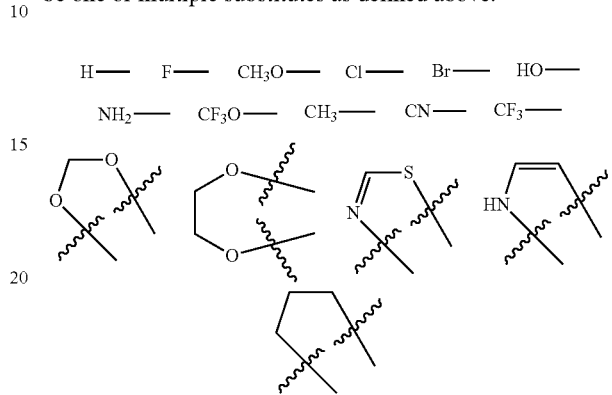

Preferred heterocyclic groups in compounds of Formula (I) include

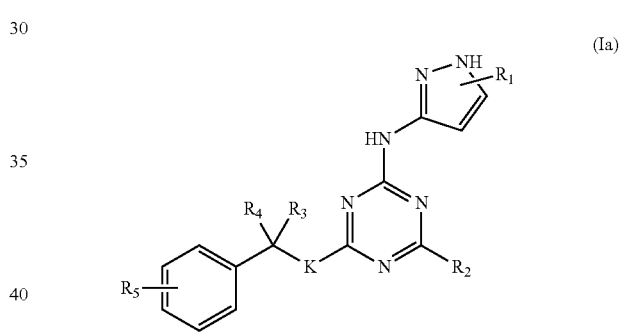

(Ia)

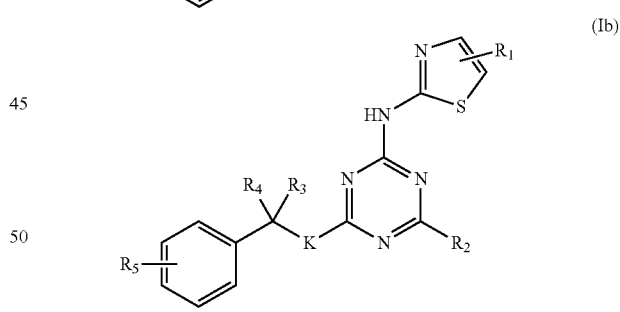

(Ib)

Which optionally may be substituted.

According to another embodiment, the present invention relates to a compound of formula (I) wherein R1 is hydrogen.

According to another embodiment, the present invention relates to a compound of formula (I) wherein R1 is chloro.

According to another embodiment, the present invention relates to a compound of formula (I) wherein R1 is methyl.

According to another embodiment, the present invention relates to a compound of formula I wherein R1 is ethyl.

According to another embodiment, the present invention relates to a compound of formula I wherein R1 is propyl.

According to another embodiment, the present invention relates to a compound of formula I wherein R1 is isopropyl.

According to another embodiment, the present invention relates to a compound of formula I wherein R1 is isobutyl.

According to another embodiment, the present invention relates to a compound of formula I wherein R1 is tert-butyl.

According to another embodiment, the present invention relates to a compound of formula I wherein R1 is cyclopropyl.

According to another embodiment, the present invention relates to a compound of formula I wherein R1 is cyclobutyl.

According to another embodiment, the present invention relates to a compound of formula I wherein R2 is methyl-piperazinyl.

According to another embodiment, the present invention relates to a compound of formula I wherein R2 is (2-hydroxy-lethyl)-piperazinyl.

According to another embodiment, the present invention relates to a compound of formula I wherein R2 is (4-pyridinyl)-piperazinyl.

According to another embodiment, the present invention relates to a compound of formula I wherein R2 is methyl.

According to another embodiment, the present invention relates to a compound of formula I wherein R2 is ethyl.

According to another embodiment, the present invention relates to a compound of formula I wherein R2 is cyclopropyl.

Examples of specific compounds of the present invention are those compounds defined in the following:

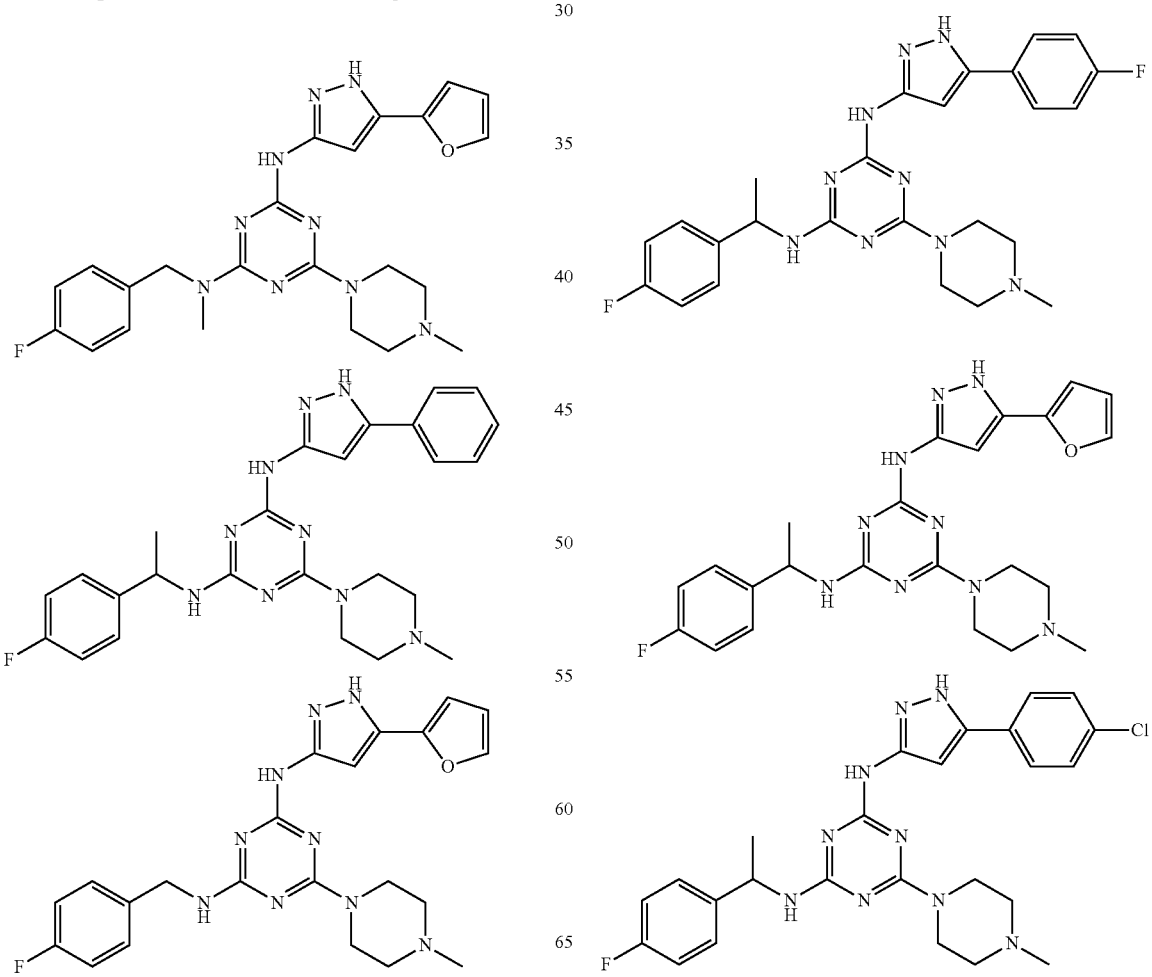

-continued

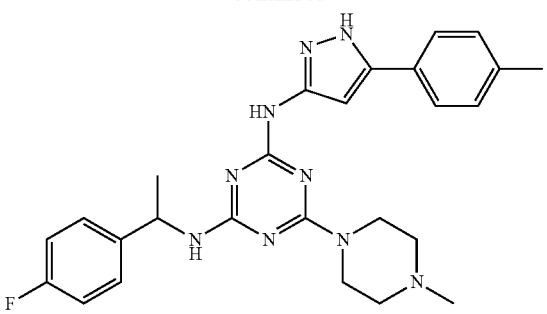

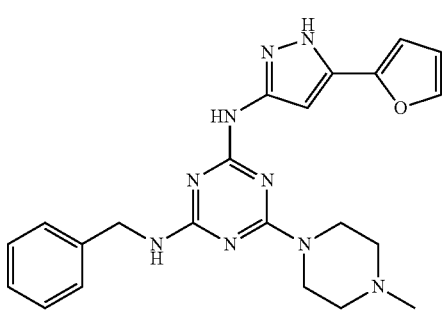

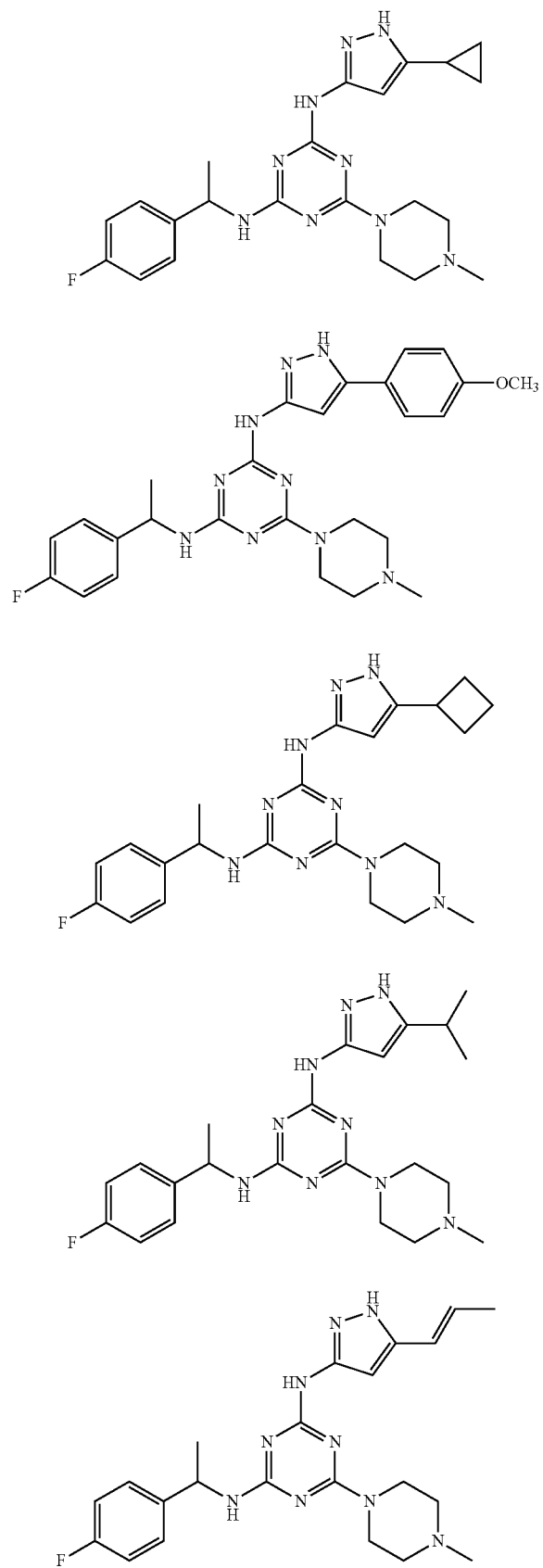
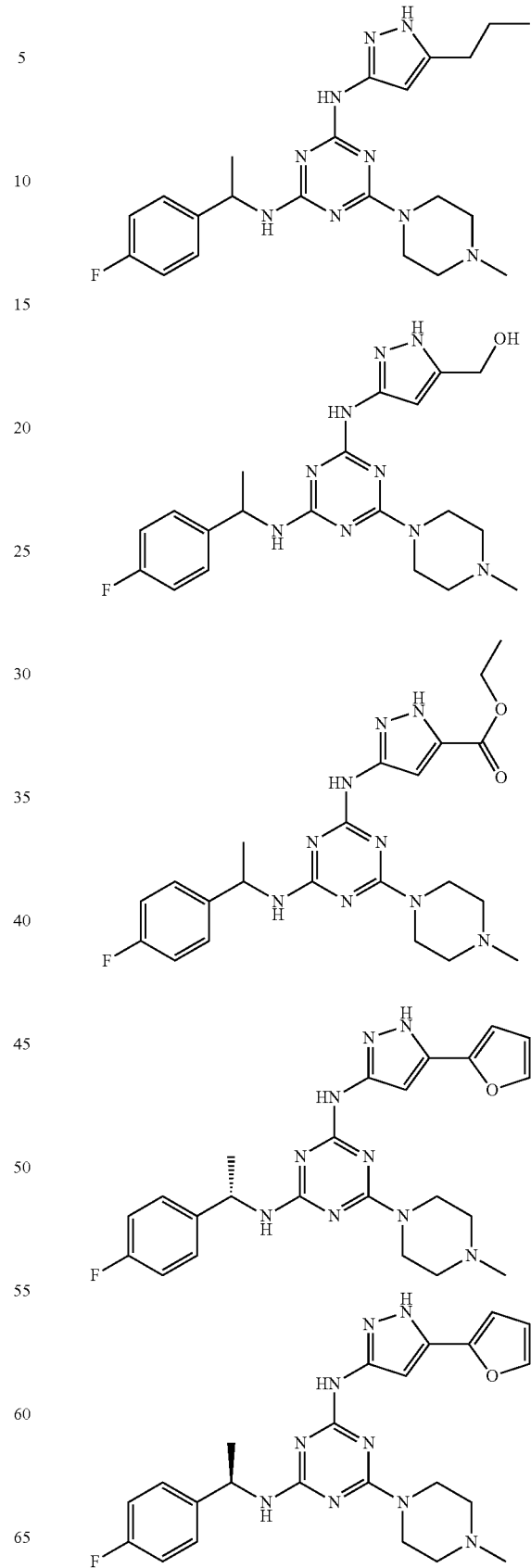

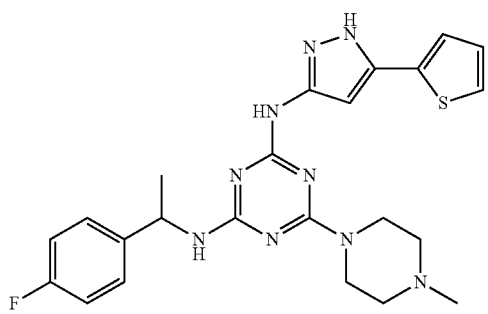
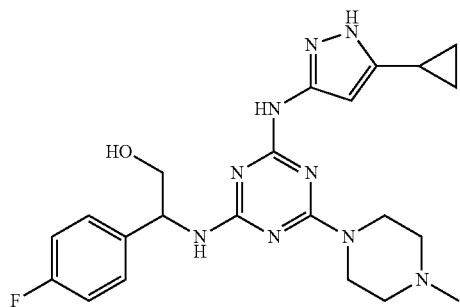
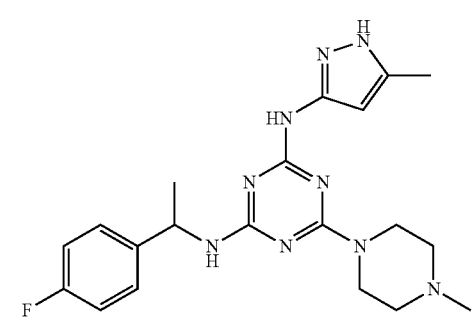
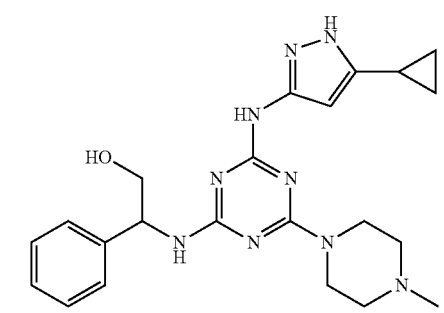
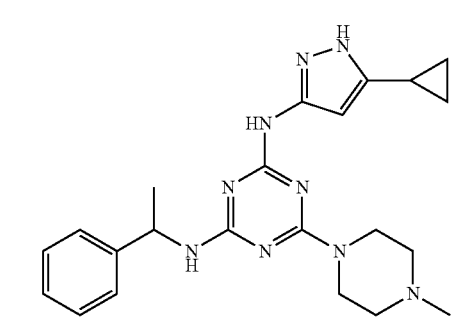
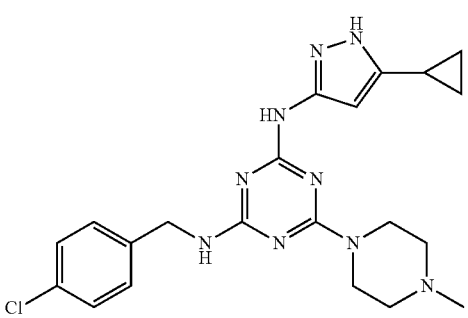
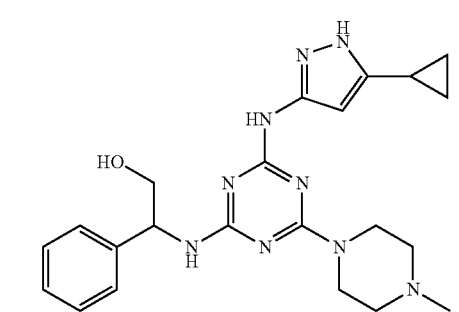
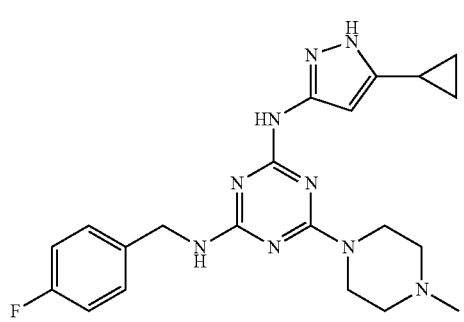
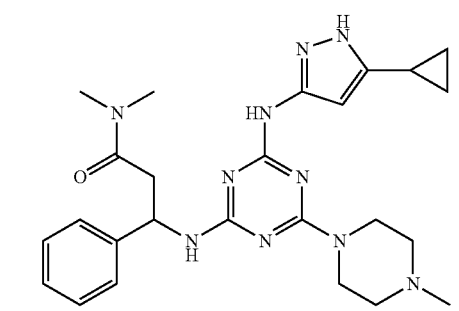
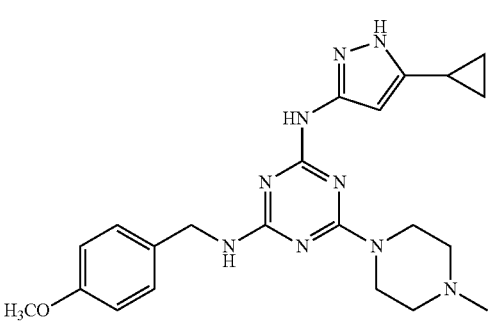

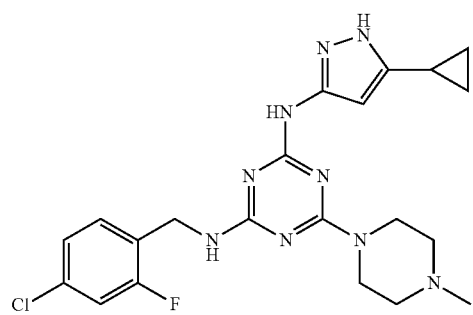
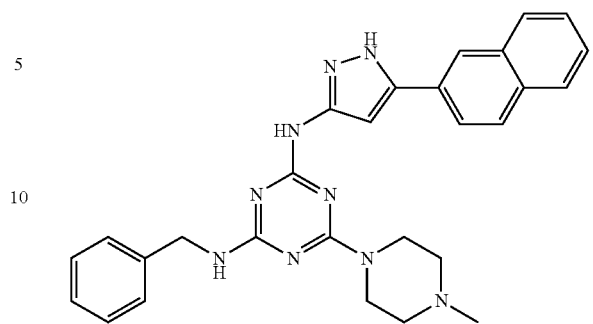
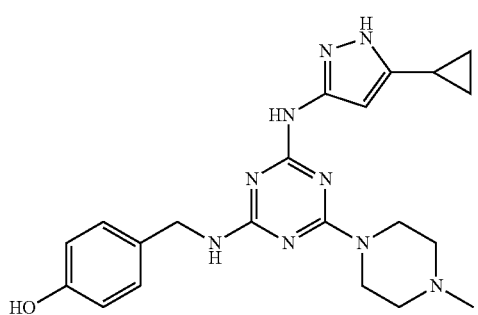
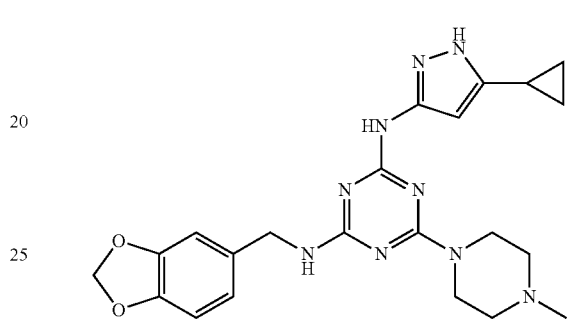
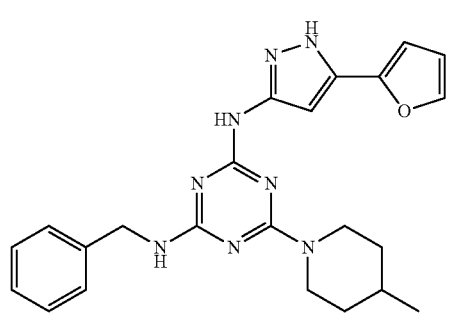
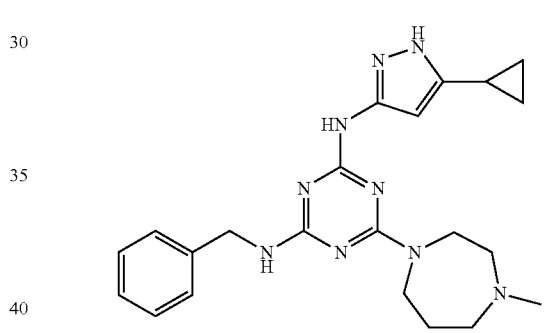
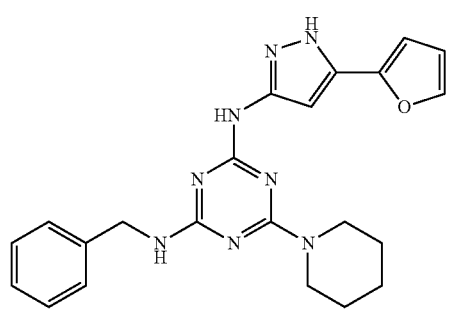
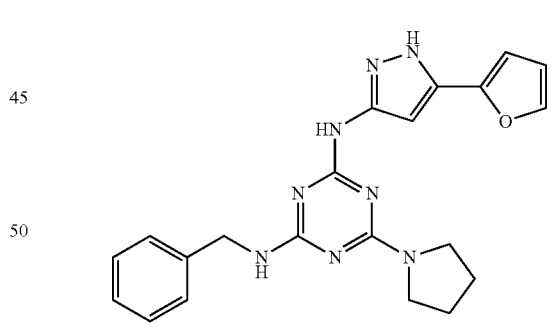
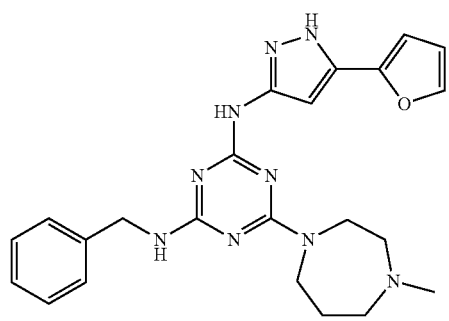
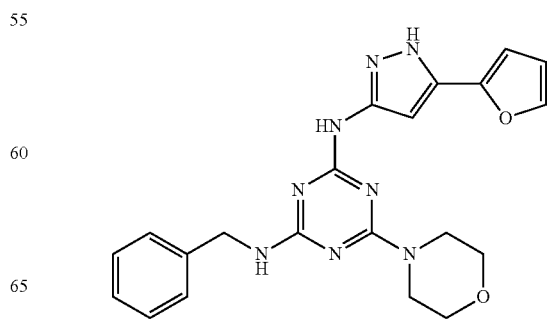

29
-continued
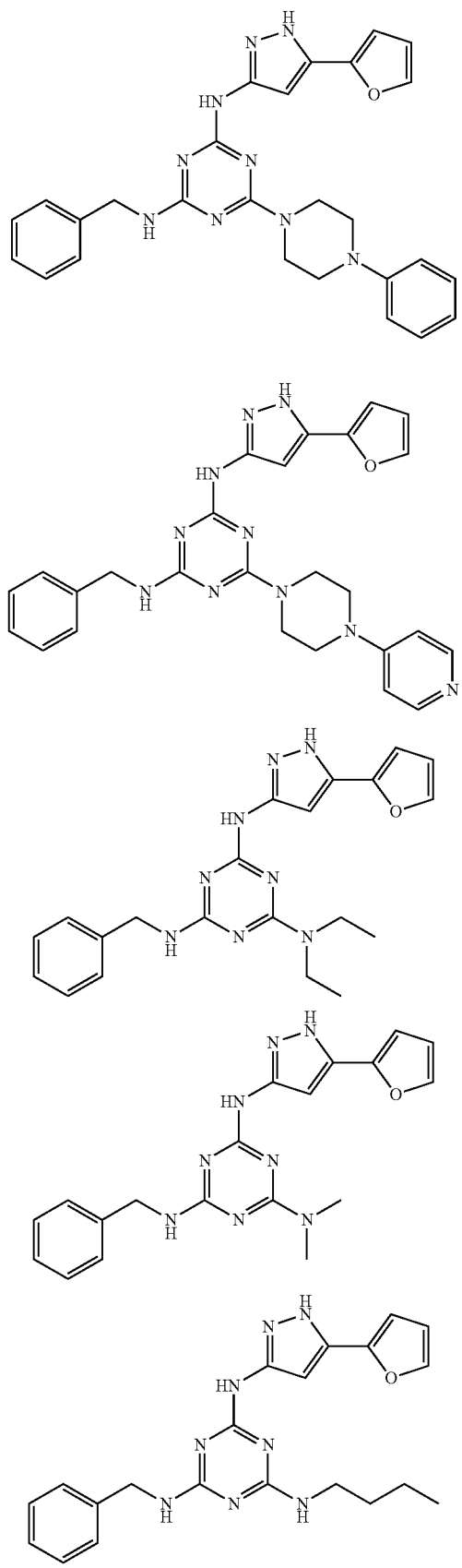
30
-continued
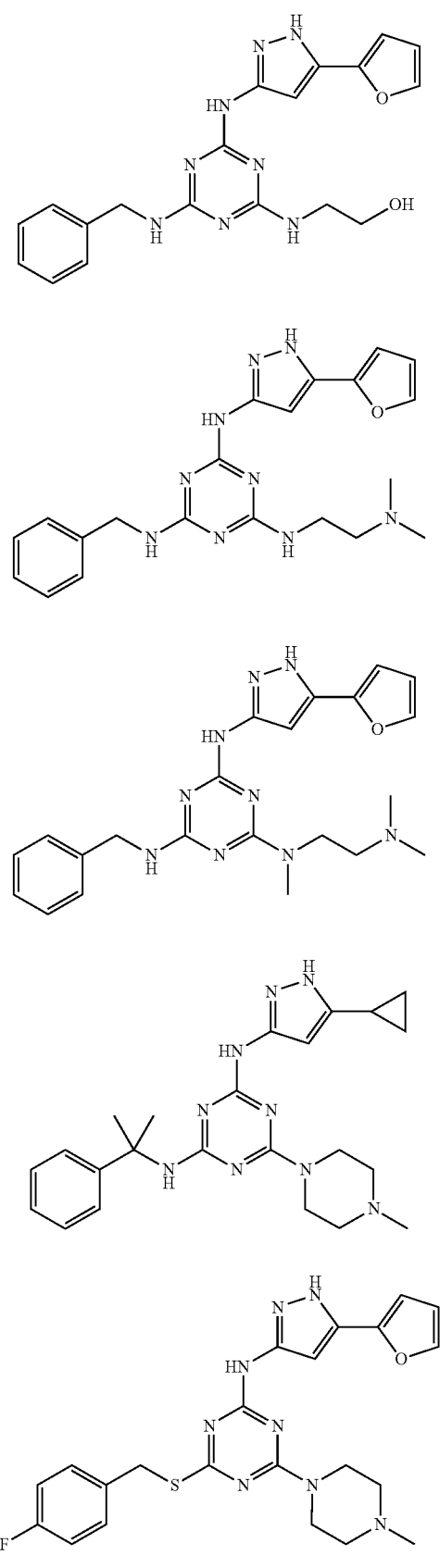

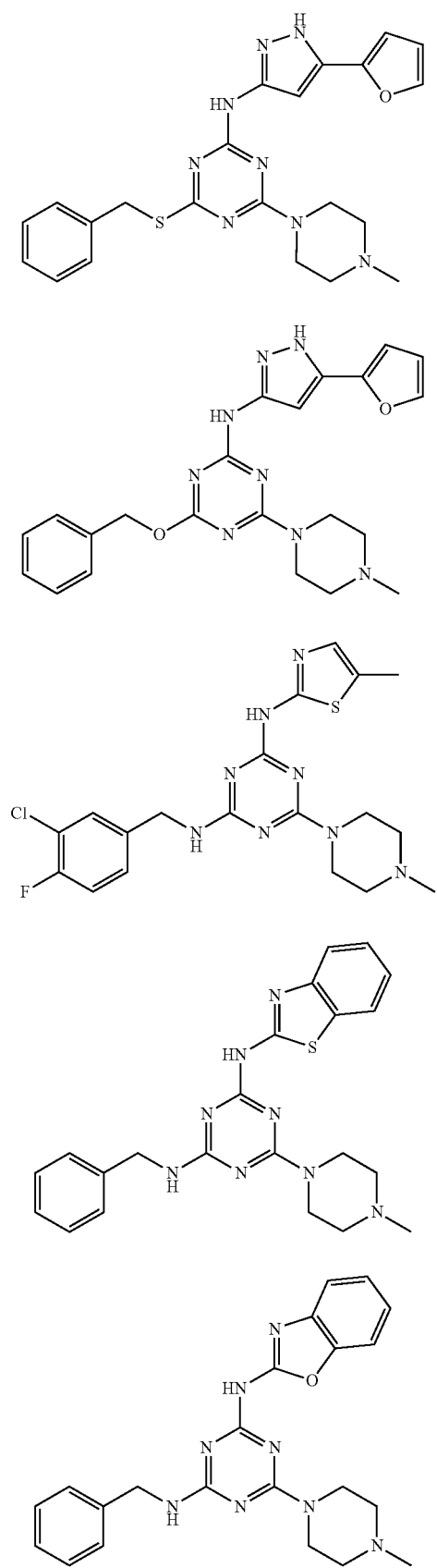
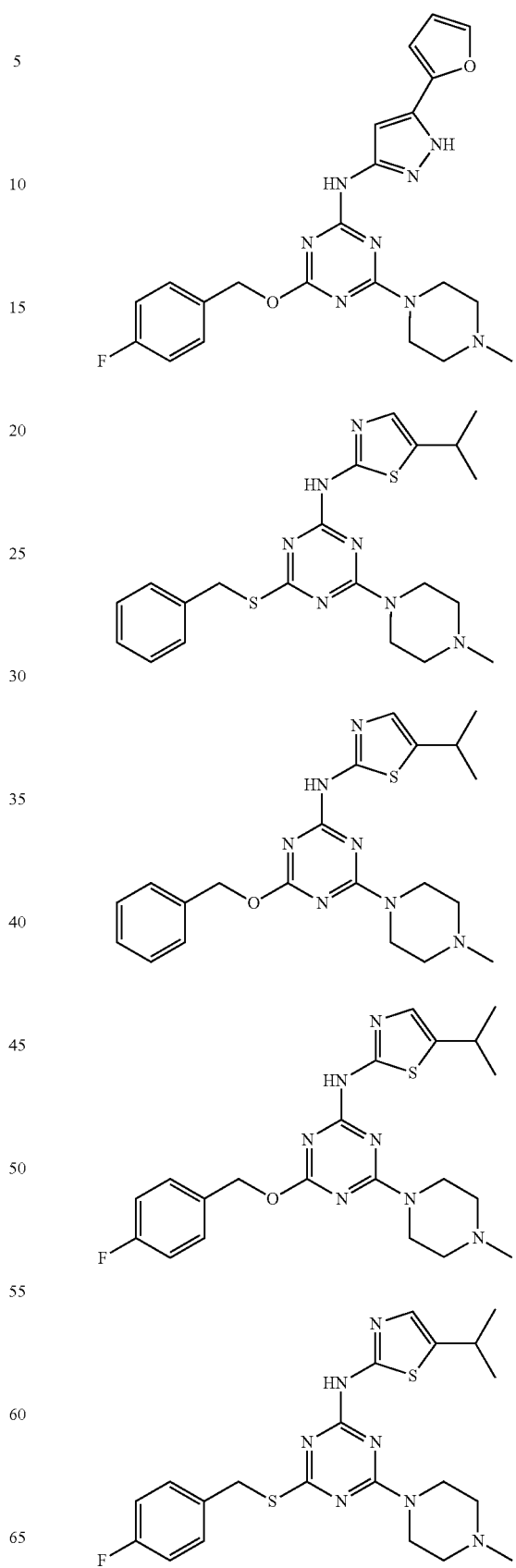

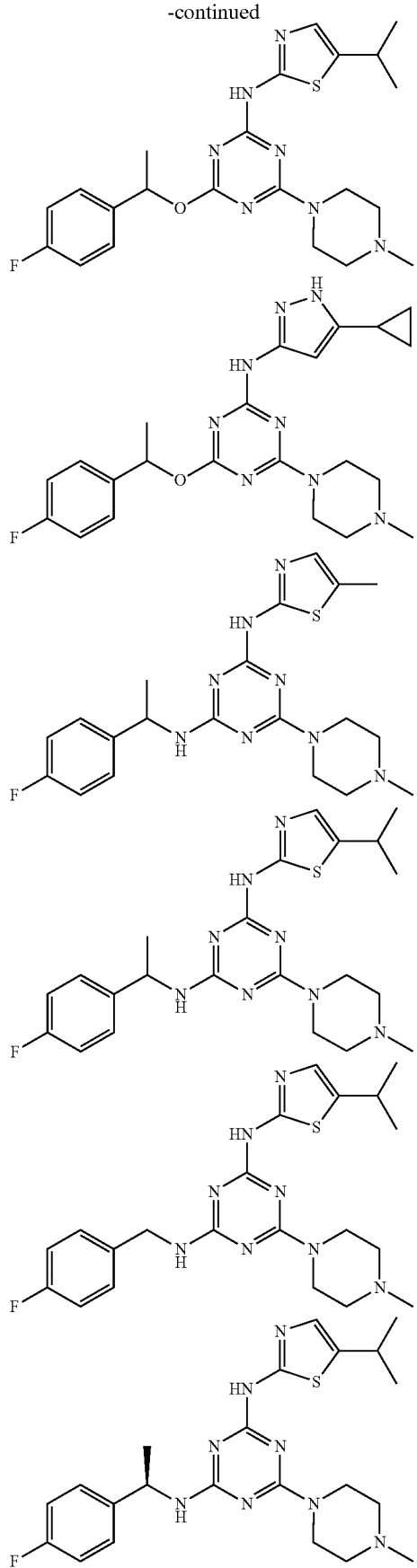
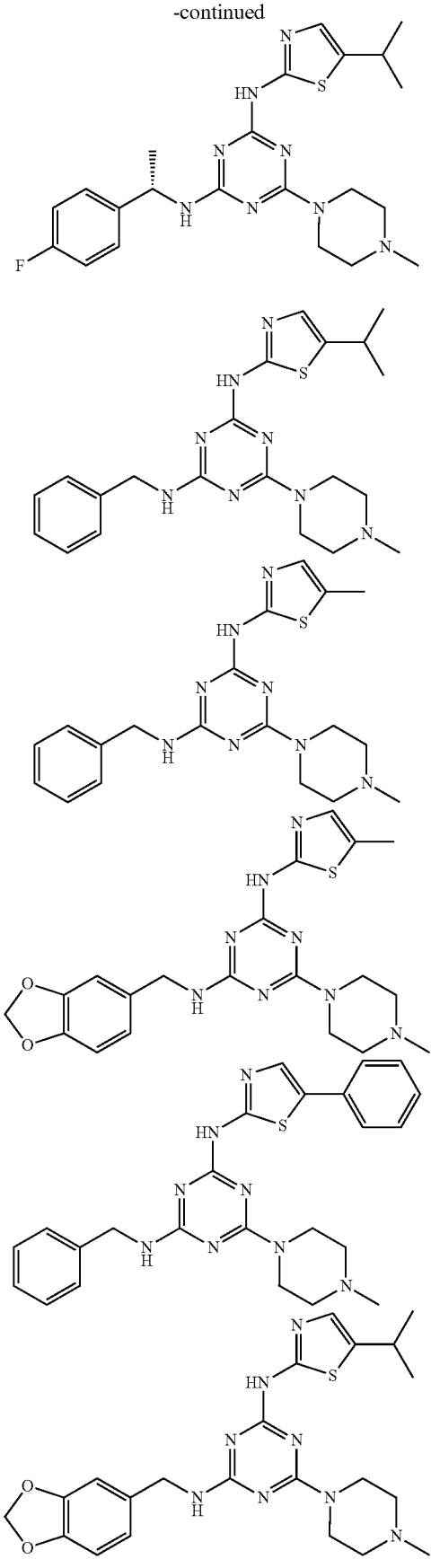

In another embodiment, a method of preparing the inventive compounds is provided. The compounds of the present invention can be generally prepared using cyanuric chloride as a starting material. Compound (I) may contain various stereoisomers, geometric isomers, tautomeric isomers, and the like. All of possible isomers and their mixtures are included in the present invention, and the mixing ratio is not particularly limited.

The triazine derivative compounds of Formula (I) in this invention can be prepared by known procedure in the prior art. The examples could be found in US patent No. 2005250945A1; US patent No. 20050227983A1; PCT WO 051007646A1; PCT WO 051007648A2; PCT WO 05/003103A2; PCT WO 05/011703A1; and J. of Med. Chem. (2004), 47(19), 4649-4652. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

In the Schemes that follow the term "reduction" refers to the process of reducing a nitro functionality to an amino functionality, or the process of transforming an ester functionality to an alcohol. The reduction of a nitro group can be carried out in a number of ways well known to those skilled in the art of organic synthesis including, but not limited to, catalytic hydrogenation, reduction with SnCl2 and reduction with titanium bichloride. The reduction of an ester group is typically performed using metal hydride reagents including, but not limited to, diisobutyl-aluminum hydride (DIBAL), lithium aluminum hydride (LAH), and sodium borohydride. For an overview of reduction methods see: Hudlicky, M. Reductions in Organic Chemistry, ACS Monograph 188, 1996. In the Schemes that follow, the term "hydrolyze" refers to the reaction of a substrate or reactant with water. More specifically, "hydrolyze" refers to the conversion of an ester or nitrite functionality into a carboxylic acid. This process can be catalyzed by a variety of acids or bases well known to those skilled in the art of organic synthesis.

The compounds of Formula (I) may be prepared by use of known chemical reactions and procedures. The following general preparative methods are presented to aid one of skill in the art in synthesizing the inhibitors, with more detailed examples being presented in the experimental section describing the working examples.

Heterocyclic amines are defined in formula (II). Some of heterocyclic amines are commercially available, others may be prepared by known procedure in the prior art (Katritzky, et al. Comprehensive Heterocyclic Chemistry; Permagon Press: Oxford, UK, 1984, March. Advanced Organic Chemistry, 3" Ed.; John Wiley: New York, 1985), or by using common knowledge of organic chemistry.

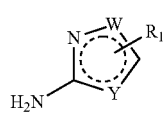
(II)

For example, substituted heterocyclic amines can be generated using standard methods (March, J. Advanced Organic Chemistry, 4th Ed.; John Wiley, New York (1992); Larock, R. C. Comprehensive Organic Transformations, $2^{nd}$ Ed., John Wiley, New York (1999); World patent No. WO 99/32106). As shown in Scheme 1, heterocyclic amines can be commonly synthesized by reduction of nitroheteros using a metal catalyst, such as Ni, Pd, or Pt, and $H_2$ or a hydride transfer agent, such as formate, cyclohexadiene, or a borohydride (Rylander. Hydrogenation Methods; Academic Press: London, UK (1985)). Nitroheteros may also be directly reduced using a strong hydride source, such as LAH, (Seyden-Penne. Reductions by the Alumino- and Borohydrides in Organic Synthesis; VCH Publishers: New York (1991)), or using a zero valent metal, such as Fe, Sn or Ca, often in acidic media. Many methods exist for the synthesis of nitroaryls (March, J. Advanced Organic Chemistry, 4th Ed.; John Wiley, New York (1992); Larock, R. C. Comprehensive Organic Transformations, $2^{nd}$ Ed., John Wiley, New York (1999))).

Scheme 1

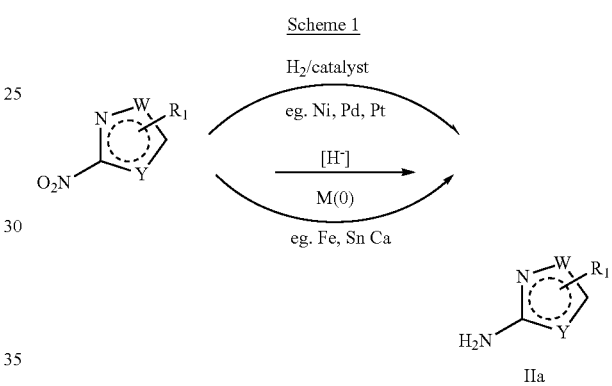

As illustrated in Scheme 2, thiazole amine with a substituent (IIb) can be prepared from commercial compounds as illustrated in Scheme 2. By route 1, a substituted aldehyde, which may be commercially available or prepared by oxidizing an alcohole, can be brominated by broming or NBS (N-Bromosuccinimide); after bromination, the aldehyde can be converted to the corresponding thiazole amine (IIb) by reacting with thiourea. For the oxidation step, a variety of oxidizing reagent can be used, such as pyridinium chlorochromate (PCC) activated dimethyl sulfoxide (DMSO), hypervalent iodide compounds, Tetrapropylammonium perruthenate (TPAP) or 2,2,6,6-Tetramethylpiperidine-1-oxyl (TEMPO). A lot of thiazole amines can be prepared by this way.

Scheme 2

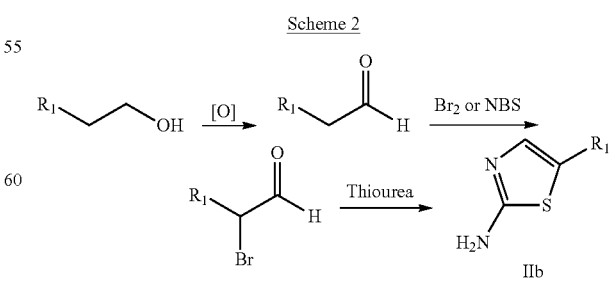

A lot of substituted pyrazole amines are commercially available and can be used directly. In some special case, pyrazole amines with a substituent (IIc) can be prepared by known procedure in the prior art, such as U.S. Pat. No. 6,407,238; F. Gabrera Escribano, et al. Tetrahedron Letters, Vol. 29, No. 46, pp. 6001-6004, 1988; *Org. Biomol. Chem.*, 2006, 4, 4158-4164; WO/2003/026666.

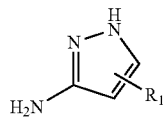

(IIc)

Precursors $R_2H$ can be purchased from suppliers such as Alderich.

Precursors $R_5PhC(R_3)(R_4)KH$ can be purchased from suppliers as exampled earlier, or synthesized from commercially available precursors using established protocols in organic synthesis.

The preparation of the compounds of formula (I) in this invention can be carried out by methods known in the art (e.g., *J. Med. Chem.* 1996, 39, 4354-4357; *J. Med. Chem.* 2004, 47, 600-611; *J. Med. Chem.* 2004, 47, 6283-6291; *J. Med. Chem.* 2005, 48, 1717-1720; *J. Med. Chem.* 2005, 48, 5570-5579; U.S. Pat. No. 6,340,683 B1; JOC, 2004, 29, 7809-7815).

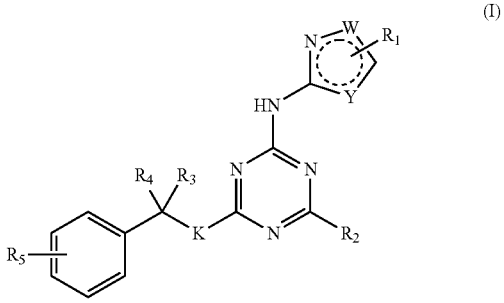

(I)

As shown in scheme 3, the triazine derivative can be synthesized by the reaction of cyanuric chloride with a sequence of heterocyclic amines to give dichlororotiazine intermediate of compound b, which can react with $R_5PhC(R_3)(R_4)KH$ to produce the advanced monochlorointermediate of compound c. The displacement of the last chlorine by $R_2H$ can be achieved by increasing the temperature, affording the trisubstituted-1,3,5-triazines (I). The reaction can be strpwise or in one pot. Alternative sequence can also be used to make triazine derivatives as illustrated in Scheme 3.

Scheme 3

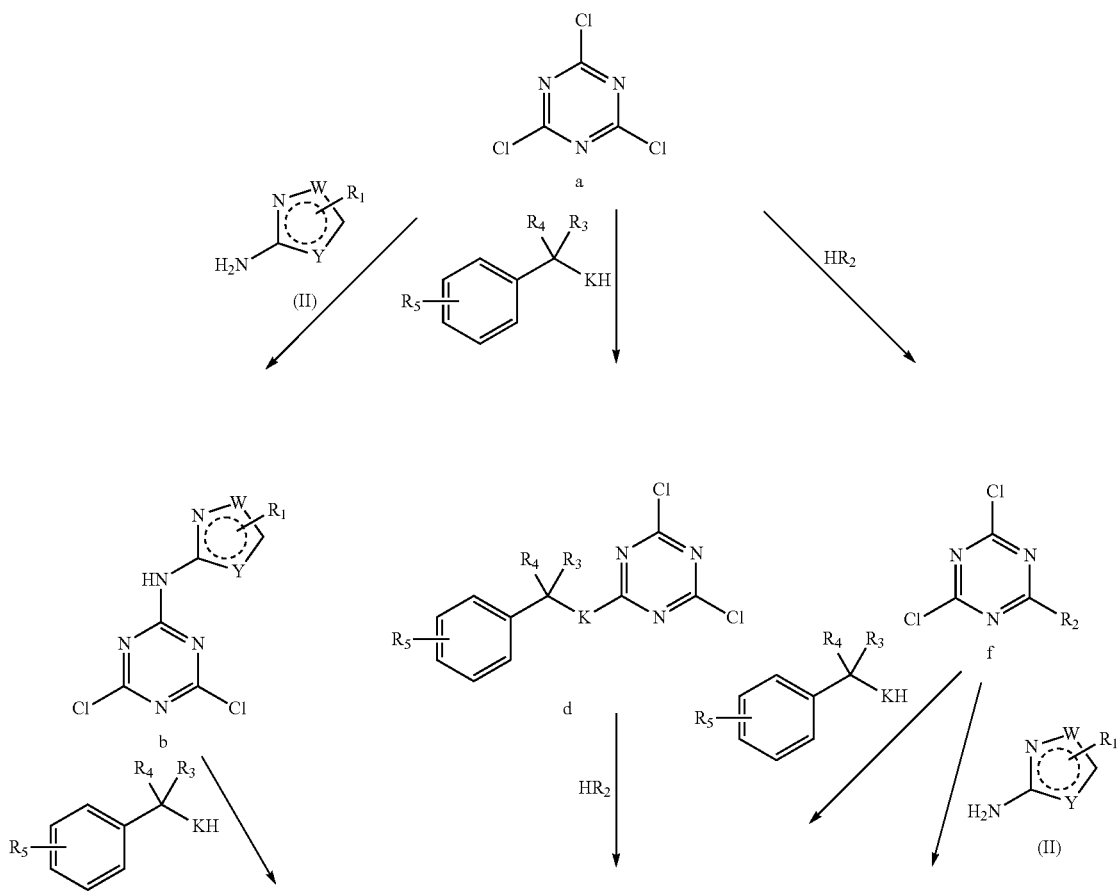

-continued

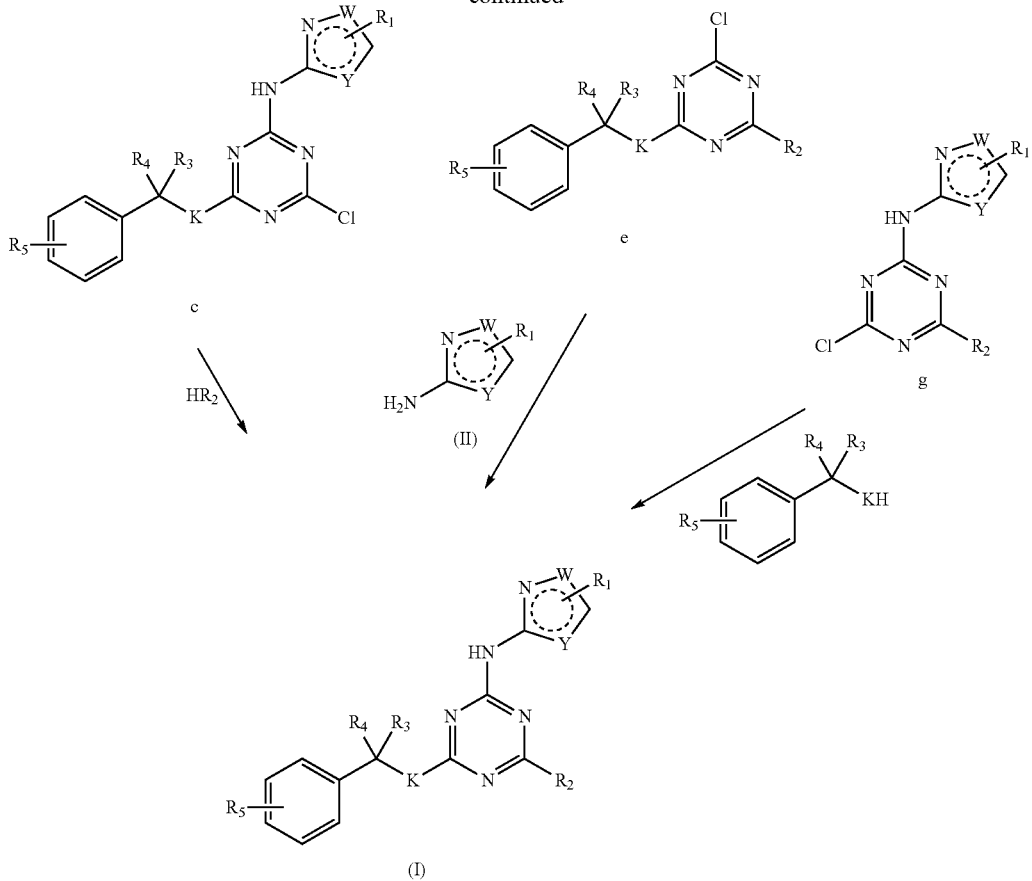

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane. dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The present invention provides compositions of matter that are formulations of one or more active drugs and a pharmaceutically-acceptable carrier. In this regard, the invention provides a composition for administration to a mammalian subject, which may include a compound of formula I, or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization. The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone) ; and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing triazine derivatives and methods useful for the in vivo delivery of triazine derivatives in the form of nanoparticles, which are suitable for any of the aforesaid routes of administration.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

In accordance with the invention, the compounds of the invention may be used to treat diseases associated with cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemialreperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; scleroderma; preeclampsia; thalassemia; Kaposi's sarcoma; von Hippel Lindau disease; and the like.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with a kinase.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with a tyrosine kinase.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with the kinase that is a serine kinase or a threonine kinase.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with the kinase that is a Src family kinase.

The invention also provides methods of treating a mammal afflicted with the above diseases and conditions. The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

In one aspect, the invention compounds are administered in combination with chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-□a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr Cancer Drug Targets (2003), 3(5), 349-58).

The exemplary therapeutical agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

EXAMPLES

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate (NaHCO3) and sodium chloride (brine) were saturated.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

Low resolution mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

High performance liquid chromatography (HPLC) was use to anaylize the purity of triazine derivatives. HPLC was performed on a Phenomenex Synergi Polar-RP, 4u, 80A, 150×4.6 mm column using a vShimadzusystem equipted with SPD-M10A Phosphodiode Array Detector.Mobile phase A was water and mobile phase B was acetonitrile with a gradient from 20% to 80% B over 60 minutes and re-equilibrate at A/B (80:20) for 10 minutes. UV detection was at 220 and 54 nm.

Example 1

(1)

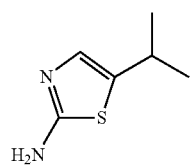

To a solution of 3-methylbutyl aldehyde (0.9 mL, 7.18 mmol) in E$_2$O (15mL) was added 5,5-dibromobarbituric acid (1.0 g, 3.59 mmol). Reaction was stirred at room temperature for 18h. Mixture was filtered, washed with ether and concentrated. Residue was washed with hexane, filtered and concentrated. Residue was dissolved in EtOH (20 mL) and thiourea was added. Mixture was refluxed for 1 d. Reaction was neutralized with 7N ammonia and concentrated. Residue was chromatographed on a silica gel column eluted with 1-10% MeOH/DCM afforded 1. $^1$H NMR (400 MHz, DMSO-d$_6$) δ6.72 (d, J=1.2 Hz, H, Ar—H), 4.96 (bs, 2H, NH$_2$), 3.03-2.96 (m, 1H, CH), 1.27 (s, 3H, CH$_3$), 1.25 (s, 3H, CH$_3$); ESI-MS: calcd for (C6H10N2S) 142, found 143 [M+H]$^+$.

Example 2

(2)

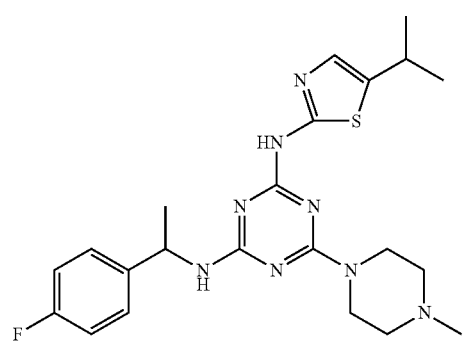

To a solution of cyanuric chloride (200 mg, 1.08 mmol) in THF (12 mL) was added a solution of 1-(4-fluorophenyl)ethanamine (154 mg, 1.08 mmol) at −15° C.-0° C. and stirred for 1.5h. DIPEA (0.09 mL, 0.49 mmol) in THF (5mL) was added and continued stirring for another 30 min. The above reaction mixture was placed in microwave vial, 5-isopropylthiazol-2-amine (compound 1) (151mg, 1.08 mmol) and DIPEA (0.09 mL, 0.49 mmol) were added. The mixture was heated at 150° C. for 10 minutes using microwave initiator. A solution of N-Methylpiperazine (163.4 mg, 1.63 mmol) and DIPEA (0.09 mL, 0.49 mmol) in THF (5 mL) was added to the above vial at room temperature. The mixture was heated at 60° C. for 0.2 h. After cooling to room temperature, saturated NaHCO$_3$ in water was added to the flask and the mixture was extracted with dichloromethane (3×25 ml) and washed by brine, dried over sodium sulfate and concentrated. The resulting crude product was purified by Teledyne-Isco flash system by using DCM/MeOH, 0 to 15% of Methanol in dichloromethane to provide compound 2 as white solids (24 mg, 8%). $^1$H NMR (400 MHz, DMSO-d$_6$) δ10.95 (s, 1H, NH), 7.85 (brs, 1H), 7.45 (m, 2H), 7.22-7.01 (m, 3H), 5.10 (m, 1H), 3.68 (m, 4H), 3.11 (m, 1H), 2.3 (m, 4H), 2.20 (s, 3H), 1.45 (m, 3H), 1.2 (m, 6H); ESI-MS: calcd for (C22H29FN8S) 456, found 457 [M+H]$^+$. HPLC: retention time: 11.10 min. purity: 84%.

Example 3

(3)

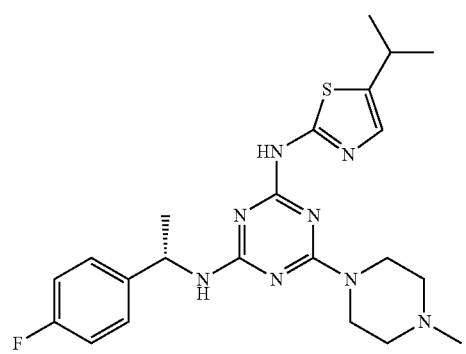

A solution of (S)-1-(4-fluorophenyl)ethanamine (214 μL, 1.63 mmol) in THF (1.0 mL) was added to a solution of cyanuric chloride (300 mg, 1.63 mmol) in THF (10.0 mL) at 0° C. The mixture was stirred at 0° C. for 15 min and then DIPEA (284 μL, 1.63 mmol) was added. The mixture was stirred at 0° C. for further 15 min. 5-Isopropylthiazol-2-amine (compound 1) (255 mg, 1.79 mmol) and DIPEA (312 μL, 1.79 mmol) were added and the mixture was subjected to microwave irradiation at 150° C. for 10 min. 1-Methylpiperazine (362 μL, 3.26 mmol) and DIPEA (568 μL, 3.26 mmol) were added and the mixture was subjected to microwave irradiation at 60° C. for 20 min. EtOAc was added and the mixture was washed with saturated NaHCO$_3$ solution and brine, respectively. The organic phase was dried over anhydrous Na$_2$SO4 and then concentrated under reduced pressure. The residue was purified by flash column chromatography on silica gel (DCM/MeOH 99:1 to 96:4 and then EtOAc/DCM/MEOH 80:15:5) to yield the compound 3 (75 mg, 10% yield) as a pale yellow solid. $^1$H NMR (400 MHz, DMSO-d$_6$, 80° C.): δ10.31 (s, 1H), 7.43 (m, 2H), 7.34 (d, J=8.0 Hz, 1H), 7.08 (m, 2H), 7.02 (m, 1H), 5.23 (s, 1H), 3.74 (m, 4H), 3.10 (m, 1H), 2.34 (m, 4H), 2.22 (s, 3H), 1.47 (d, J=6.8 Hz, 3H), 1.28 (d, J=6.8 Hz, 6H). MS (ESI): Calcd. for C$_{22}$H$_{30}$FN$_8$S: 457, found 457 (M+H)$^+$ Example 4

(4)

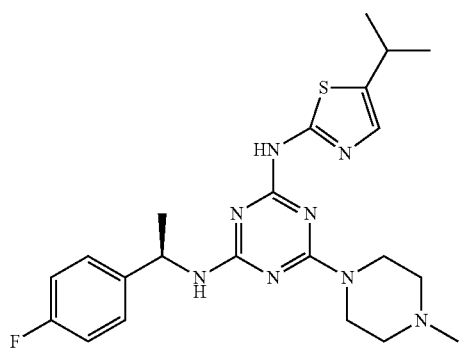

A solution of (R)-1-(4-fluorophenyl)ethanamine (214 μL, 1.63 mmol) in THF (1.0 mL) was added to a solution of cyanuric chloride (300 mg, 1.63 mmol) in THF (10.0 mL) at 0° C. The mixture was stirred at 0° C. for 15 min and then DIPEA (284 μL, 1.63 mmol) was added. The mixture was stirred at 0° C. for further 15 min. 5-isopropylthiazol-2-amine (Compound 1) (255 mg, 1.79 mmol) and DIPEA (312 μL, 1.79 mmol) were added and the mixture was subjected to microwave irradiation at 150° C. for 10 min. 1-Methylpiperazine (362 μL, 3.26 mmol) and DIPEA (568 μL, 3.26 mmol) were added and the mixture was subjected to microwave irradiation at 60° C. for 20 min. EtOAc was added and the mixture was washed with saturated NaHCO$_3$ solution and brine, respectively. The organic phase was dried over anhydrous Na$_2$SO$_4$ and then concentrated under reduced pressure. The residue was purified by flash column chromatography on silica gel (DCM/MeOH 99:1 to 96:4 and then EtOAc/DCM/MEOH 80:15:5) to yield the compound 4 (68 mg, 9% yield) as a pale yellow solid. $^1$H NMR (400 MHz, DMSO-d$_6$, 80° C.): δ10.31 (s, 1H), 7.43 (m, 2H), 7.34 (d, J=8.0 Hz, 1H), 7.08 (m, 2H), 7.02 (m, 1H), 5.23 (s, 1H), 3.74 (m, 4H), 3.10 (m, 1H), 2.34 (m, 4H), 2.22 (s, 3H), 1.47 (d, J=6.8 Hz, 3H), 1.28 (d, J=6.8 Hz, 6H). MS (ESI): Calcd. for C$_{22}$H$_{30}$FN$_8$S: 457, found 457 (M+H)$^+$ Example 5

(5)

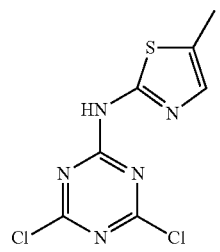

A solution of 2-amino-5-methylthiazol (1.30 g, 13.56 mmol) and DIPEA (2.00 mL, 11.48 mmol) in THF (55 ml,) was added dropwise to a stirred solution of cyanuric chloride (2.50 g, 13.56 mmol) in THF (70 mL) at –5° C. After the addition was complete, the reaction mixture was stirred at –5 C for 15 more minute. During the stirring, large amount of yellow precipitate formed, which was collected by filtration, wahed with THF (3×20 mL), ethyl acetate (3×20 mL) and hexanes (1×10 mL). The compound (2.72 g, 91%) was used directly for further reaction without purification.

Example 6

(6)

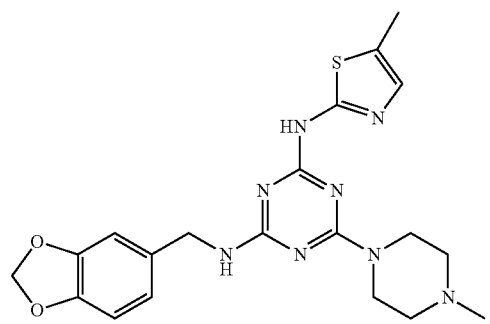

To a solution of compound 5 (0.200 mg, 0.76 mmol) in DMF (5 mL) was added a solution of benzo[d][1,3]dioxol-5-ylmethanamine (0.115 mg, 0.76 mmol) and DIPEA (0.16 mL, 0.916 mmol) in DMF (5 mL) dropwise at —15° C. After addition, the mixture was stirred at 0 ° C.-Rt for 4 hours. A solution of 1-methylpiperazine (153 mg, 1.53 mmol) DIPEA (0.16 mL, 0.916 mmol) was added to the above reaction flak at room temperature. The mixture was stirred at room temperature for overnight. Water (5-8mL) was added to the reaction flask, and the resulting precipitate was filtered and washed with EtOAc (10 mL) to provide compound 6 as white solids (0.050 g, 15%). $^1$H NMR (400 MHz, DMSO-d$_6$) δ10.85 (br s, 1H), 7.60 (br s, 1H), 6.95 (m, 4H), 5.98 (m, 2H), 4.35 (m, 2H), 3.72 (m, 4H), 2.25 (m, 10H); ESI-MS: calcd for (C20H24N802S) 440, found 441 (MH$^+$). HPLC: retention time: 11.11 min, purity: 95%.

Example 7

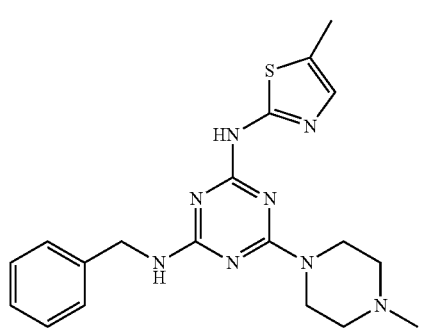

(7)

To a solution of compound 5 (0.200 mg, 0.76 mmol) in DMF (5 mL) was added a solution of benzylamine (0.89 mg, 0.76 mmol) and DIPEA (0.16 mL, 0.916 mmol) in DMF (5 mL) dropwise at −15° C. After addition, the mixture was stirred at 0° C.-Rt for 4 hours. A solution of 1-methylpiperazine (153 mg, 1.53 mmol) DIPEA (0.16 mL, 0.916 mmol) was added to the above reaction flak at room temperature. The mixture was stirred at room temperature for overnight. Water (5-8 mL) was added to the reaction flask, and the resulting precipitate was filtered and washed with EtOAc (10mL) to provide compound 7 as white solids (0.054 g, 18%). $^1$H NMR (400 MHz, DMSO-$d_6$) δ10.80 (br s, 1H), 7.60 (br s, 1H), 7.35 (m, 4H), 7.22 (m, 1H), 7.01 (s, 1H), 4.61 (m, 1H), 4.45 (m, 1H), 4.35 (m, 2H), 3.75 (m, 4H), 2.25 (m, 10H); ESI-MS: calcd for (C19H24N8S) 396 found 397 (MH$^+$).

Example 8

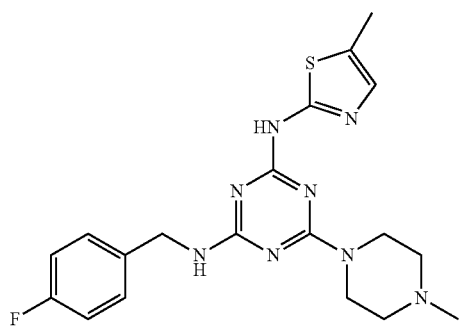

(8)

To a solution of compound 5 (0.200 mg, 0.76 mmol) in DMF (5 mL) was added a solution of 4-fluorobenzylamine (0.95 mg, 0.76 mmol) and DIPEA (0.16 mL, 0.916 mmol) in DMF (5 mL) dropwise at −15° C. After addition, the mixture was stirred at 0° C.-Rt for 4 hours. A solution of 1-methylpiperazine (153 mg, 1.53 mmol) DIPEA (0.16 mL, 0.916 mmol) was added to the above reaction flak at room temperature. The mixture was stirred at room temperature for overnight. Water (5-8mL) was added to the reaction flask, and the resulting precipitate was filtered and washed with EtOAc (10 mL) to provide compound 8 as white solids (0.086 g, 27%). NMR (400 MHz, DMSO-$d_6$) δ10.80 (br s, 1H), 7.70(br s, 1H), 7.35 (m, 2H), 7.12 (m, 2H), 6.98 (s, 1H), 4.49 (m, 1H), 4.38 (m, 1H), 3.75 (m, 4H), 2.30 (m, 7H), 2.15 (s, 3H); ESI-MS: calcd for (C19H23FN8S) 414 found 415 (MH$^+$). HPLC: retention time: 10.89 min, purity: 90%.

Example 9

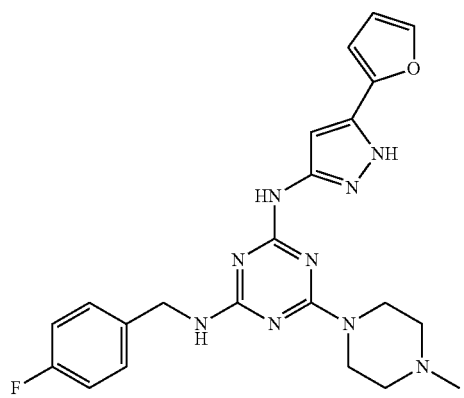

(9)

To a solution of cyanuric chloride (300 mg, 1.63 mmol) in THF (16 mL) was added 3-amino-5-(2-furyl)pyrazole (243 mg, 1.63 mmol) and DIPEA (0.21 mL, 1.63 mmol) at 0° C. The reaction mixture was let to stir at 0° C. to room temperature for 2 h. 1-methylpiperazine (0.12 mL, 1.63 mmol) and DIPEA (0.21 mL, 1.63 mmol) were added to the above mixture and allowed to stir at room temperature for 3 hours. 4-fluorobenzylamine (0.37 mL, 3.26 mmol) and DIPEA (0.57 mL, 2.26 mmol) were added to the mixture and the mixture was stirred at room temperature overnight. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 9 as light yellow solid (66 mg, 9%). NMR (400 MHz, DMSO-$d_6$) δ12.61 (bs, 1H, NH), 9.90 (bs, 1H, NH), 9.14-9.01 (d, 1H, NH), 7.83-5.96 (m, 8H, Ar-H), 4.45 (bs, 2H, CH$_2$), 3.67 (bs, 4H, 2CH$_2$), 2.28 (bs, 4H, 2CH$_2$), 2.17 (s, 3H, CH$_3$); ESI-MS: calcd for (C22H24FN9O) 449, found 450 [M+11]$^+$. HPLC: retention time: 16.58 min. purity: 100%.

Example 10

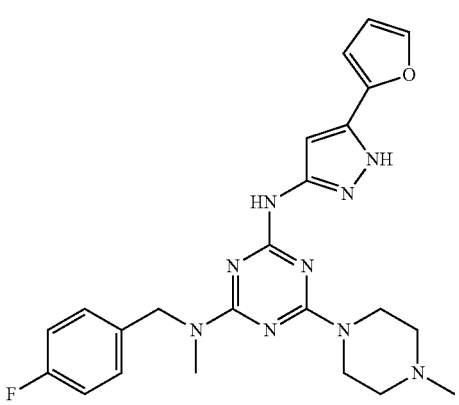

(10)

To a solution of cyanuric chloride (300 mg, 1.63 mmol) in THF (16 mL) was added 3-amino-5-(2-furyl)pyrazole (243 mg, 1.63 mmol) and DIPEA (0.21 mL, 1.63 mmol) at 0° C.

The reaction mixture was let to stir at 0° C. to room temperature for 2 h. 1-methylpiperazine (0.12 mL, 1.63 mmol) and DIPEA (0.21 mL, 1.63 mmol) were added to the above mixture and allowed to stir at room temperature for 3 hours. 4-fluoro-N-methyl-benzylamine (0.43 mL, 3.26 mmol) and DIPEA (0.57 mL, 2.26 mmol) were added to the mixture and the mixture was stirred at room temperature overnight. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 10 as light yellow solid (90 mg, 12%). $^1$H NMR (400 MHz, DMSO-d$_6$) δ12.63 (bs, 1H, NH), 9.28 (bs, 1H, NH), 7.70 (s, 1H, Ar—H), 7.35-7.09 (m, 5H, Ar—H), 6.72-6.58 (m, 2H, Ar—H), 4.78 (s, 2H, CH$_2$), 3.71 (bs, 4H, 2CH$_2$), 3.04 (s, 3H, CH$_3$), 2.32 (bs, 4H, 2CH$_2$), 2.20 (s, 3H, CH$_3$); ESI-MS: calcd for (C23H26FN9O) 463, found 464 [M+H]$^+$. HPLC: retention time: 19.98 min. purity: 97%.

Example 11

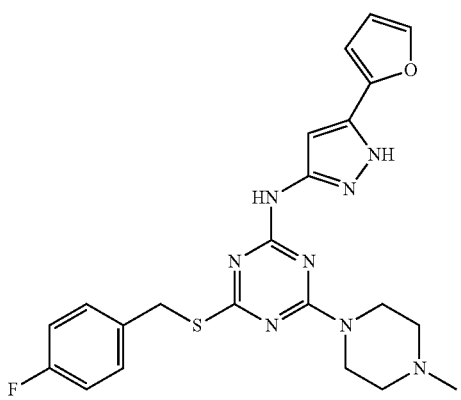

(11)

To a solution of cyanuric chloride (300 mg, 1.63 mmol) in THF (16 mL) was added 3-amino-5-(2-furyl)pyrazole (243 mg, 1.63 mmol) and DIPEA (0.21 mL, 1.63 mmol) at 0° C. The reaction mixture was let to stir at 0° C. to room temperature for 2 h. 1-methylpiperazine (0.12 mL, 1.63 mmol) and DIPEA (0.21 mL, 1.63 mmol) were added to the above mixture and allowed to stir at room temperature for 3 hours. 4-fluorobenzyl mercaptan (0.40 mL, 3.26 mmol) and DIPEA (0.57 mL, 2.26 mmol) were added to the mixture and the mixture was stirred at room temperature overnight. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 11 as light yellow solid (530 mg, 70%). $^1$H NMR (400 MHz, DMSO-d$_6$) δ12.84 (s, 1H, NH), 9.94 (bs, 1H, NH), 7.75 (bs, 1H, Ar—H), 7.47 (bs, 2H, Ar—H), 7.12 (t, J=8.8 Hz, 2H, Ar—H), 6.77-6.59 (m, 3H, Ar—H), 4.34 (s, 2H, CH$_2$), 3.74 (bs, 4H, 2CH$_2$), 2.34 (bs, 4H, 2CH$_2$), 2.20 (s, 3H, CH$_3$); ESI-MS: calcd for (C23H26FN9O) 466, found 467 [M+H]$^+$. HPLC: retention time: 21.31 min. purity: 97%.

Example 12

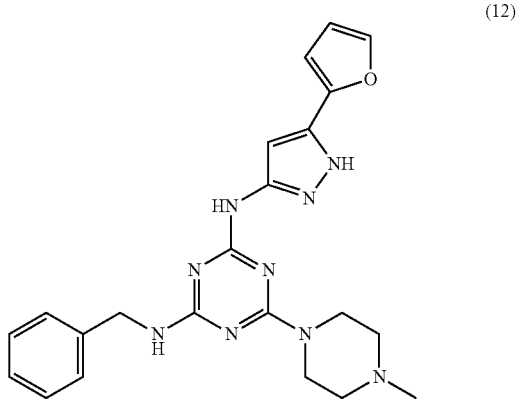 [SMILES: CN1CCN(c2nc(NCc3ccccc3)nc(Nc3cc(-c4ccco4)[nH]n3)n2)CC1]

(12)

To a solution of cyanuric chloride (300 mg, 1.63 mmol) in THF (16 mL) was added benzylamine (0.18 mL, 1.63 mmol) and DIPEA (0.21 mL, 1.63 mmol) at 0° C. The reaction mixture was let to stir at 0° C. to room temperature for 2 h. 3-amino-5-(2-furyl)pyrazole (243 mg, 1.63 mmol) and DIPEA (0.21 mL, 1.63 mmol) were added to the above mixture and the resulting mixture was heated with microwave initiator at 150° C. for 10 minutes. 1-methylpiperazine (0.36 mL, 3.26 mmol) and DIPEA (0.57 mL, 3.26 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 12 as white solid (90 mg, 13%). $^1$H NMR (400 MHz, DMSO-d$_6$) δ12.62 (s, 1H, NH), 9.92 (bs, 1H, NH), 9.14 (bs, 1H, NH), 7.84-6.53 (m, 8H, Ar—H), 5.98 (bs, 1H, Ar—H), 4.49 (s, 2H, CH$_2$), 3.70 (s, 4H, 2CH$_2$), 2.30 (s, 4H, 2CH$_2$), 2.19 (s, 3H, CH$_3$); ESI-MS: calcd for (C22H24N9O) 431, found 432 [M+H]$^+$. HPLC: retention time: 29.47 min. purity: 99%.

Example 13

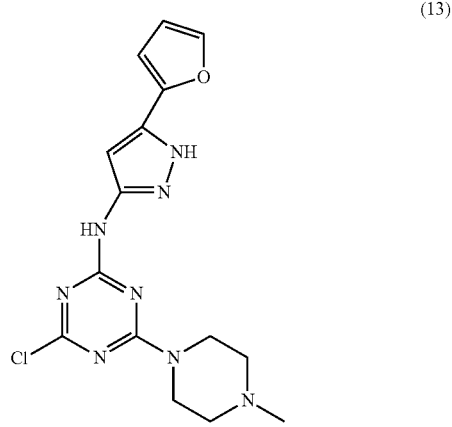 [SMILES: CN1CCN(c2nc(Cl)nc(Nc3cc(-c4ccco4)[nH]n3)n2)CC1]

(13)

To a solution of cyanuric chloride (200 mg, 1.09 mmol) in THF (16.0 mL) was added dropwise a solution of 3-amino-5-(2-furyl)pyrazole (162 mg, 1.09 mmol) and DIPEA (0.19 mL, 1.09 mmol) in THF (5 mL) at 0° C. The reaction mixture was let to stir at 0° C. to room temperature for 2 h. 1-metyl piperazine (0.12 mL, 1.09 mmol) and DIPEA (0.19 mL, 1.30 mmol) were added to the mixture. The mixture was allowed to stir at room temperature for 3 h. The solids were filtered off to give compound 13 as white solid (110 mg, 14%). %). $^1$H NMR (400 MHz, DMSO-d$_6$) δ12.92 (s, 1H, NH), 10.38 (s, 1H, NH), 7.76 (s, 1H, Ar—H), 6.81-6.61 (m, 3H, Ar—H), 3.77-3.72 (m, 4H, 2CH$_2$), 2.38-2.35 (m, 4H, 2CH$_2$), 2.21 (2, 3H, CH$_3$); ESI-MS: calcd for (C15H17ClN8O) 360, found 361 [M+H]$^+$.

Example 14

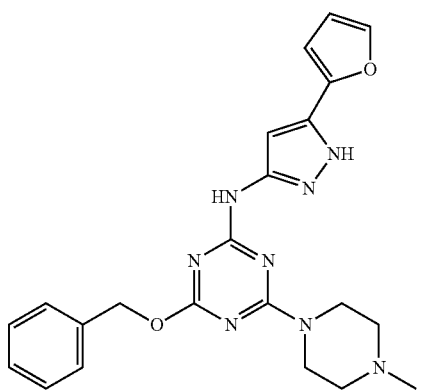

(14)

To a solution of benzyl alcohol (0.04 mL, 0.42 mmol) in DMF (5.0 mL) was added NaH (34 mg, 1.4 mmol) and reaction was stirred for 20 min. The solution of compound 13 in DMF (4.0 mL) was added dropwise a solution to the reaction mixture and it was let to stir at 60° C. overnight. Mixture was washed with water and extracted by DCM (3×50 mL). The combined organic was washed by brine, dried over sodium sulfate and concentrated. The residue was purified with DCM/MeOH mixture to give 27 as off white solid (60 mg, 50%). %). $^1$H NMR (400 MHz, DMSO-d$_6$) δ12.79 (s, 1H, NH), 9.78 (s, 1H, NH), 7.75 (bs, 1H, Ar—H), 7.46-6.74 (m, 7H, Ar—H), 6.59 (bs, 1H, Ar—H), 5.35 (s, 2H, CH$_2$), 3.73 (bs, 4H, 2CH$_2$), 2.33 (bs, 4H, 2CH$_2$), 2.20 (2, 3H, CH$_3$); ESI-MS: calcd for (C22H24N8O2) 432, found 433 [M+H]$^+$. HPLC: retention time: 16.30 min. purity: 99%.

Example 15

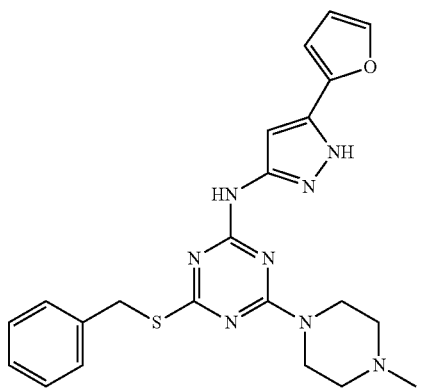

(15)

To a solution of cyanuric chloride (300 mg, 1.63 mmol) in THF (16 mL) was added benzylmercaptan (0.19 mL, 1.63 mmol) and DIPEA (0.21 mL, 1.63 mmol) at 0° C. The reaction mixture was let to stir at 0° C. to room temperature for 2 h. 3-amino-5-(2-furyppyrazole (243 mg, 1.63 mmol) and DIPEA (0.21 mL, 1.63 mmol) were added to the above mixture and the resulting mixture was heated with microwave initiator at 150° C. for 10 minutes. 1-methylpiperazine (0.36 mL, 3.26 mmol) and DIPEA (0.57 mL, 3.26 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 15 as white solid (250 mg, 34%). $^1$H NMR (400 MHz, DMSO-d$_6$) δ12.83 (s, 1H, NH), 9.92 (bs, 1H, NH), 7.74-6.59 (m, 9H, Ar-H), 4.34 (s, 2H, CH$_2$), 3.75 (s, 4H, 2CH$_2$), 2.34 (s, 4H, 2CH$_2$), 2.29 (s, 3H, CH$_3$); ESI-MS: calcd for (C22H24N8OS) 448, found 449 [M+H]$^+$. HPLC: retention time: 20.34 min. purity: 99%.

Example 16

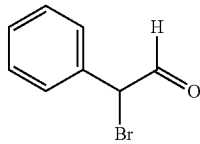

(16)

Bromine (0.92 mL, 18.00 mmol) was added dropwise to a solution of phenyl acetaldehyde (2.0 mL, 17.12 mmol) in 1,4-dioxane/Et$_2$O (30 mL, 1:1). Reaction mixture was stirred at room temperature for 1h. The reaction mixture was poured into CH$_2$Cl$_2$ (45 mL) and sodium hydrogen carbonate (3.0 g, 36 mmol) was added and stirred for 16 h. The solids were filtered off and the filtrate was concentrated to give compound 16 (3.0 g). The crude brown oil was used in the next step without further purification.

Example 17

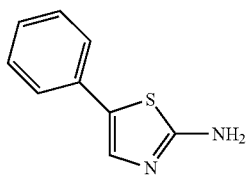

(17)

Compound 16 (3.0 g, 15.05 mmol) was added to a suspension of thiourea (1.4 g, 18.10 mmol) in ethanol. The reaction mixture was refluxed for 8 h. After cooling, solvent was concentrated and residue was subjected to purification with DCM/MeOH to give 17 as yellow solid (2.3 g , 80%). $^1$H NMR (400 MHz, DMSO-d$_6$) δ9.37 (bs, 2H, NH$_2$), 7.82 (s, 1H, Ar—H), 7.58-7.34 (m, 6H, Ar—H); ESI-MS: calcd for (C9H8N2S) 176, found 177 [M+H]$^+$.

Example 18

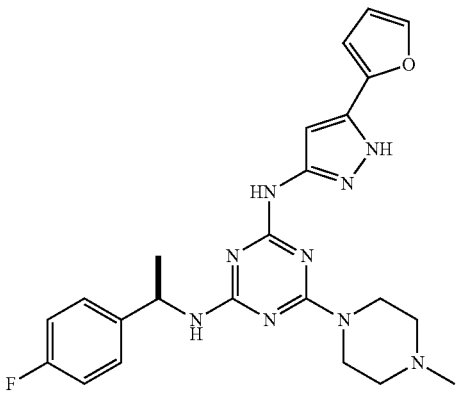

(18)

To a solution of cyanuric chloride (230 mg, 1.25 mmol) in THF (16 mL) was added 4-fluorophenyl-2-ethylamine (0.16 mL, 1.25 mmol) and DIPEA (0.20 mL, 1.25 mmol) at 0° C. The reaction mixture was let to stir at 0° C. to room temperature for 2 h. 3-amino-5-(2-furyl)pyrazole (187 mg, 1.25 mmol) and DIPEA (0.20 mL, 1.25 mmol) were added to the above mixture and the resulting mixture was heated with microwave initiator at 150° C. for 10 minutes. 1-methylpiperazine (0.28 mL, 2.50 mmol) and DIPEA (0.44 mL, 2.50 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 18 as white solid (65 mg, 11%). $^1$H NMR (400 MHz, DMSO-d$_6$, 80° C.) δ12.48 (bs, 1H, NH), 9.52 (bs, 1H, NH), 8.55 (bs, 1H, NH), 7.71-5.96 (m, 8H, Ar—H), 5.12 (bs, 1H, CH), 3.67 (b, 4H, 2CH$_2$), 2.30 (bs, 4H, 2CH$_2$), 2.21 (s, 3H, CH$_3$), 1.47 (s, 3H, CH$_3$), 1.45 (s, 3H, CH$_3$); ESI-MS: calcd for (C23H26FN9O) 463, found 464 [M+H]$^+$. HPLC: retention time: 16.82 min. purity: 95%.

Example 19

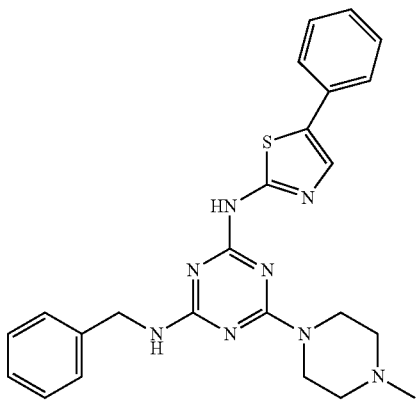

(19)

To a solution of cyanuric chloride (230 mg, 1.25 mmol) in THF (16 mL) was added benzylamine (0.14 mL, 1.25 mmol) and DIPEA (0.20 mL, 1.25 mmol) at 0° C. The reaction mixture was let to stir at 0 ° C. to room temperature for 2 h. 3-amino-5-phenylthiazole (compound 17) (220 mg, 1.25 mmol) and DIPEA (0.20 mL, 1.25 mmol) were added to the above mixture and the resulting mixture was heated with microwave initiator at 150° C. for 10 minutes. 1-methylpiperazine (0.28 mL, 2.50 mmol) and DIPEA (0.44 mL, 2.50 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 19 as white solid (16 mg, 3%). $^1$H NMR (400 MHz, DMSO-d$_6$) δ12.56 (bs, 1H, NH), 9.20 (bs, 1H, NH), 7.75-5.96 (m, 9H, Ar—H), 3.71 (bs, 4H, 2CH$_2$), 2.33 (s, 4H, 2CH$_2$), 2.21 (s, 3H, CH$_3$); ESI-MS: calcd for (C24H26N8S) 458, found 459 [M+H]$^+$. HPLC: retention time: 7.89 min. purity: 97%.

Example 20

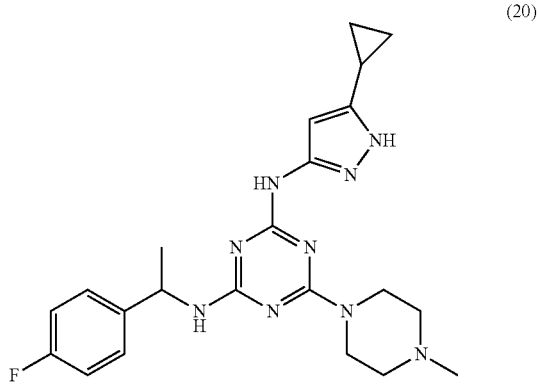 [SMILES: CC(Nc1nc(Nc2cc(C3CC3)[nH]n2)nc(N2CCN(C)CC2)n1)c1ccc(F)cc1]

(20)

To a solution of cyanuric chloride (230 mg, 1.25 mmol) in THF (16 mL) was added 4-fluorophenyl-2-ethylamine (0.16 mL, 1.25 mmol) and DIPEA (0.20 mL, 1.25 mmol) at 0° C. The reaction mixture was let to stir at 0 ° C. to room temperature for 2 h. 3-cyclopropyl-1-H-pyrazol-5-amine (154 mg, 1.25 mmol) and DIPEA (0.20 mL, 1.25 mmol) were added to the above mixture and the resulting mixture was heated with microwave initiator at 150° C. for 10 minutes. 1-methylpiperazine (0.28 mL, 2.50 mmol) and DIPEA (0.44 mL, 2.50 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 20 as off white solid (135 mg, 25%). $^1$H NMR (400 MHz, DMSO-d$_6$) δ8.18 (d, 1H, NH), 7.42-6.76 (m, 5H, Ar—H), 5.10-5.03 (m, 1H, CH), 3.73-3.66 (m, 4H, 2CH$_2$), 2.33-2.30 (m, 4H, 2CH$_2$), 2.19 (s, 3H, CH$_3$), 1.77-1.70 (m, 1H, CH), 1.41 (d, 3H, CH$_3$), 0.83-0.80 (m, 2H, Ar—H), 0.60-0.58 (m, 2H, Ar—H) ; ESI-MS: calcd for (C22H28FN9) 437, found 438 [M+H]$^+$. HPLC: retention time: 7.80 min. purity: 94%.

Example 21

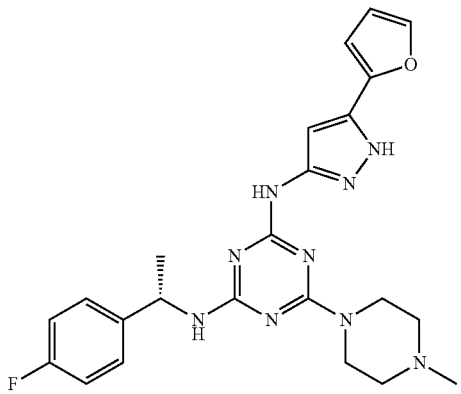

To a solution of cyanuric chloride (230 mg, 1.25 mmol) in THF (16 mL) was added (S)-1-(4-fluorophenyl)ethylamine (0.16 mL, 1.25 mmol) and DIPEA (0.20 mL, 1.25 mmol) at 0° C. The reaction mixture was let to stir at 0° C. to room temperature for 2 h. 3-amino-5-(2-furyl)pyrazole (187 mg, 1.25 mmol) and DIPEA (0.20 mL, 1.25 mmol) were added to the above mixture and the resulting mixture was heated with microwave initiator at 150° C. for 10 minutes. 1-methylpiperazine (0.28 mL, 2.50 mmol) and DIPEA (0.44 mL, 2.50 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 21 as light brown solid (52 mg, 9%). $^1$H NMR (400 MHz, DMSO-d$_6$, 80° C.) δ 12.46 (bs, 1H, NH), 9.52 (bs, 1H, NH), 8.55 (bs, 1H, NH), 7.63-6.04 (m, 8H, Ar—H), 5.12 (bs, 1H, CH), 3.67 (bs, 4H, 2CH$_2$), 2.30 (bs, 4H, 2CH$_2$), 2.21 (s, 3H, CH$_3$), 1.47 (s, 3H, CH$_3$), 1.45 (s, 3H, CH$_3$); ESI-MS: calcd for (C23H26FN9O) 463, found 464 [M+H]$^+$. HPLC: retention time: 17.10 min purity: 99%.

Example 22

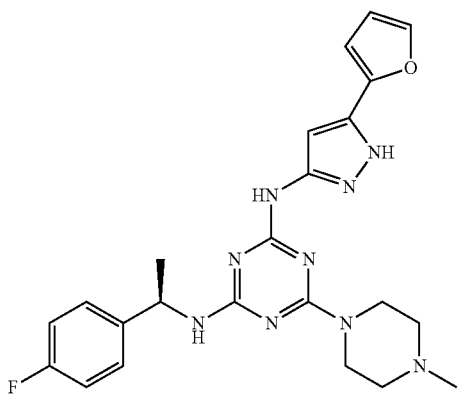

To a solution of cyanuric chloride (230 mg, 1.25 mmol) in THF (16 mL) was added (R)-1-(4-fluorophenyl)-2-ethylamine (0.16 mL, 1.25 mmol) and DIPEA (0.20 mL, 1.25 mmol) at 0° C. The reaction mixture was let to stir at 0° C. to room temperature for 2 h. 3-amino-5-(2-furyl)pyrazole (187 mg, 1.25 mmol) and DIPEA (0.20 mL, 1.25 mmol) were added to the above mixture and the resulting mixture was heated with microwave initiator at 150° C. for 10 minutes. 1-methylpiperazine (0.28 mL, 2.50 mmol) and DIPEA (0.44 mL, 2.50 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 22 as white solid as light brown solid (88 mg, 15%). $^1$H NMR (400 MHz, DMSO-d$_6$, 80° C.) δ12.48 (bs, 1H, NH), 9.53 (bs, 1H, NH), 8.58 (bs, 1H, NH), 7.65-6.04 (m, 8H, Ar—H), 5.12 (bs, 1H, CH), 3.68 (bs, 4H, 2CH$_2$), 2.34 (bs, 4H, 2CH$_2$), 2.23 (s, 3H, CH$_3$), 1.47 (s, 3H, CH$_3$), 1.45 (s, 3H, CH3); ESI-MS: calcd for (C23H26FN9O) 463, found 464 [M+H]$^+$. HPLC: retention time: 16.62 min. purity: 95%.

Example 23

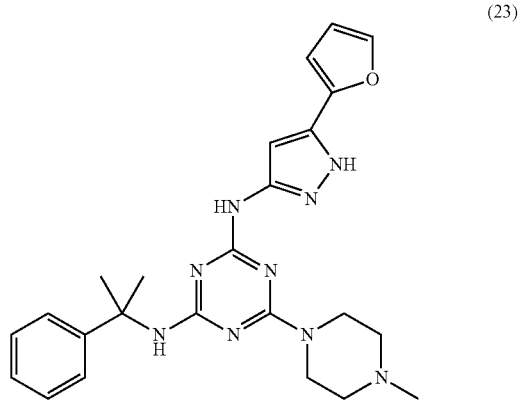 [SMILES: CN1CCN(c2nc(Nc3cc(-c4ccco4)[nH]n3)nc(NC(C)(C)c3ccccc3)n2)CC1]

To a solution of cyanuric chloride (230 mg, 1.25 mmol) in THF (16 mL) was added cumylamine (0.18 mL, 1.25 mmol) and DIPEA (0.20 mL, 1.25 mmol) at 0° C. The reaction mixture was let to stir at 0° C. to room temperature for 2 h. 3-amino-5-(2-furyl)pyrazole (187 mg, 1.25 mmol) and DIPEA (0.20 mL, 1.25 mmol) were added to the above mixture and the resulting mixture was heated with microwave initiator at 150° C. for 10 minutes. 1-methylpiperazine (0.28 mL, 2.50 mmol) and DIPEA (0.44 mL, 2.50 mmol) were added to the mixture and the mixture was heated with microwave initiator at 60° C. for 10 minutes. Saturated NaHCO$_3$ in water was added and the mixture was extracted by ethyl acetate (3×50 mL). The combined organic was washed by brine, dried over sodium sulfate and concentrated. The residue was chromatographed on a silica gel column eluted with 0-5% MeOH/DCM afforded 23 as light brown solid (140 mg, 24%). $^1$H NMR (400 MHz, DMSO-d$_6$) δ 12.88 (bs, 1H, NH), 9.87 (bs, 1H, NH), 7.88 (bs, 1H, NH), 7.67-5,91 (m, 9H, Ar—H), 3.52-3.20 (m, 4H, 2CH$_2$), 2.32-1.96 (m, 7H, 2CH$_2$, CH$_3$), 1.67 (s, 3H, CH$_3$), 1.49 (s, 3H, CH$_3$); ESI-MS: calcd for (C24H29N9O) 459, found 460 [M+H]$^+$. HPLC: retention time: 19.16 mM. purity: 99%.

Example 24

This example illustrated c-Src kinase, Aurora-A kinase, Flt3 kinase, Ret kinase and TrkA Kinase Assays of selected Compounds from this invention (referred to Daniele Fancelli et al, J. Med. Chem., 2006, 49 (24), pp 7247-7251). The KinaseProfiler™ Service Assay Protocols (Millipore) were used to test the kinase inhibiting activity of novel compounds from this invention. To do this, the buffer composition was as: 20 mM MOPS, 1 mM EDTA, 0.01% Brij-35, 5% Glycerol, 0.1% β-mercaptoethanol, 1 mg/mL BSA. Test compounds were initially dissolved in DMSO at the desired concentration, then serially diluted to the kinase assay buffer. In a final reaction volume of 25 µL, Aurora-A(h) (5-10 mU) is incubated with 8 mM MOPS pH 7.0, 0.2 mM EDTA, 200 µM LRRASLG (Kemptide), 10 mM MgAcetate and [γ$^{33}$P-ATP]. The reaction was initiated by the addition of the MgATP mix. After incubation for 40 minute at room temperature, the reaction was stopped by addition of 5 µL of a 3% phosphoric acid solution. 10 µL of the reaction was then spotted onto a P30 filtermat and washed three times for 5 minutes in 50 mM phosphoric acid and once in methanol prior to drying and scintillation counting. Wells containing substrate but no kinase and wells containing a phosphopeptide control were used to set 0% and 100% phosphorylation value, repectively.

Also Kinase Hotspot$^{SM}$ kinase assay was used to test the compounds for IC50 or % inhibitions (Reaction Biology Corp.). Inhibitor IC50 values were determined by titration of compound at the optimal kinase concentration (Kinase EC50).

Table 1 shows representative data for the inhibition of c-Src kinase, Aurora-A kinase, Flt3 kinase, Ret kinase and TrkA Kinase by the compounds of this invention at a concentration of 1 µM.

Tabbel 1

| Example No. | % Inhibition @1 µM | | | | |
|---|---|---|---|---|---|
| | cSrc | Auroro-A | Flt3 | Ret | TrkA |
| 2 | >90 | <50 | >90 | <50 | >90 |
| 3 | >90 | 50~90 | >90 | 50~90 | >90 |
| 4 | 50~90 | <50 | >90 | <50 | 50~90 |
| 6 | 50~90 | 50~90 | >90 | 50~90 | >90 |
| 7 | 50~90 | 50~90 | >90 | >90 | >90 |
| 8 | 50~90 | 50~90 | >90 | 50~90 | >90 |
| 9 | 50~90 | <50 | >90 | <50 | >90 |
| 10 | 50~90 | 50~90 | >90 | <50 | >90 |
| 11 | 50~90 | 50~90 | >90 | <50 | >90 |
| 12 | 50~90 | <50 | >90 | <50 | >90 |
| 14 | <50 | <50 | >90 | <50 | >90 |
| 15 | <50 | <50 | >90 | <50 | >90 |
| 18 | >90 | <50 | >90 | >90 | >90 |
| 19 | <50 | <50 | <50 | <50 | <50 |
| 20 | 50~90 | 50~90 | 50~90 | <50 | 50~90 |
| 21 | <50 | <50 | >90 | >90 | >90 |
| 22 | >90 | <50 | >90 | >90 | >90 |
| 23 | <50 | <50 | >90 | >90 | >90 |

What is claimed is:
1. A compound of the formula

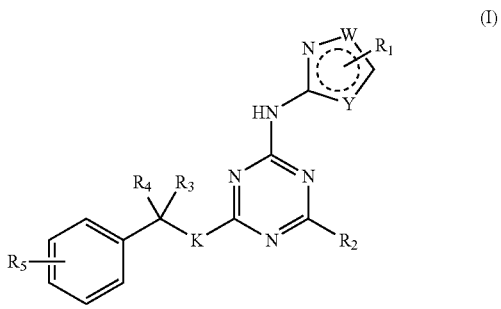

or a pharmaceutically acceptable salt thereof, wherein:
W and Y are independently selected from S, O, NR$_6$, or CR$_6$
R6 is independently selected from hydrogen or an optionally substituted C1-4 aliphatic group;
K is selected from —NR6, O, or S;
R$_1$ represents hydrogen, halogen, hydroxy, amino, cyano, alkyl, cycloalkyl, alkenyl, alkynyl, alkylthio, aryl, arylalkyl, heterocyclic, heteroaryl, heterocycloalkyl, alkylsulfonyl, alkoxycarbonyl and alkylcarbonyl;
R$_2$ is selected from:
(i) $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$alkyl, $C_1$-$C_6$ haloalkyl, each of which is substituted with from 0 to 4 substituents independently chosen from halogen, hydroxy, cyano, amino, —COOH and oxo;
(ii) amino, alkyl amino, aryl amino, heteroaryl amino;
(iii) groups of the formula (Ia):

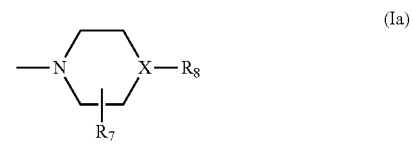

wherein:
R$_7$ represents hydrogen, $C_1$-$C_4$ alkyl, oxo;
X is CH, when R$_8$ is hydrogen; or X—R$_8$ is O; or X is N, R$_8$ represents groups of hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino$C_0$-$C_4$alkyl, (4- to 7-membered heterocycle)$C_0$-$C_4$alkyl, $C_1$-$C_6$ alkylsulfonyl, mono- and di-($C_1$-$C_6$ alkyl) sulfonamido, and mono- and di-($C_1$-$C_6$alkyl)aminocarbonyl, each of which is substituted with from 0 to 4 substituents independently chosen from halogen, hydroxy, cyano, amino, —COOH and oxo;
R$_3$ and R$_4$ are independently selected from: Hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$cycloalkyl)$C_1$-$C_4$alkyl, $C_1$-$C_6$ haloalkyl, hydroxy, cyano, amino, —COOH and oxo;
R$_5$ is 0 to 5 substituents independently chosen from:
(i) halogen, hydroxy, amino, amide, cyano, —COOH, —SO$_2$NH$_2$, oxo, nitro and alkoxycarbonyl; and
(ii) $C_1$-$C_6$ alkyl, $C_1$-$C_6$alkoxy, $C_3$-$C_{10}$ cycloalkyl, $C_2$-$C_6$ alkenyl, $C_2$-$C_6$ alkynyl, $C_2$-$C_6$ alkanoyl, $C_1$-$C_6$ haloalkyl, $C_1$-$C_6$ haloalkoxy, mono- and di-($C_1$-$C_6$alkyl) amino, $C_1$-$C_6$ alkylsulfonyl, mono- and di-($C_1$-$C_6$alkyl) sulfonamido and mono- and di-($C_1$-$C_6$alkyl)aminocarbonyl; phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, oxo, imino, $C_1$-$C_4$alkyl, $C_1$-$C_4$alkoxy and $C_1$-$C_4$haloalkyl.

2. A process for making a compound of claim 1 or its pharmaceutically acceptable salts, hydrates, solvates, and individual diastereomers thereof.

3. A pharmaceutical composition comprising at least one compound of claim 1 or its pharmaceutically acceptable salts, hydrates, solvates, and individual diastereomers thereof, and a pharmaceutically acceptable carrier.

4. The composition according to claim 3, further comprising an additional therapeutic agent.

5. A compound selected from the group consisting of:

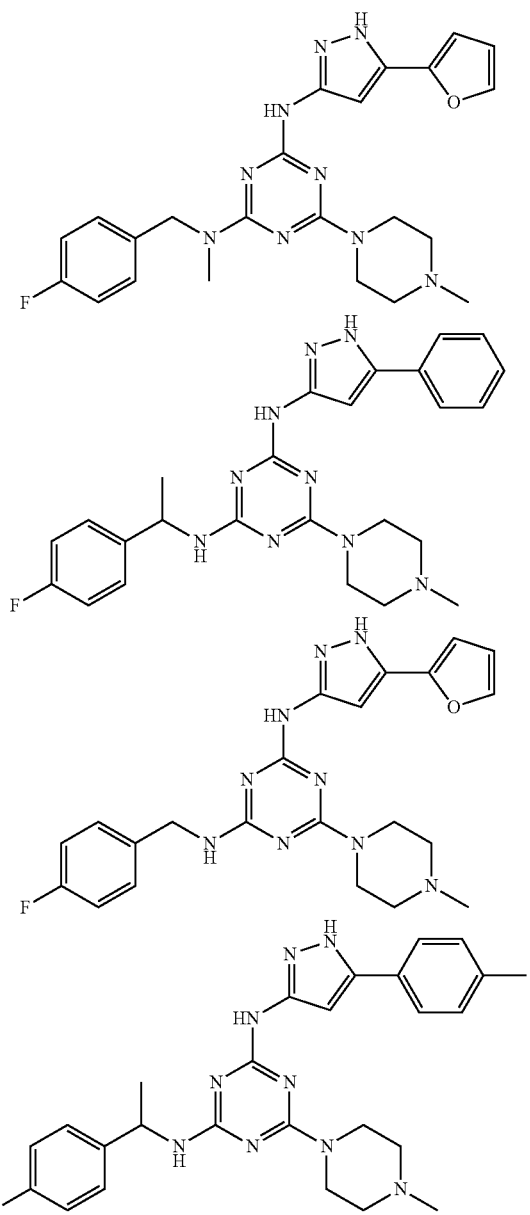

-continued

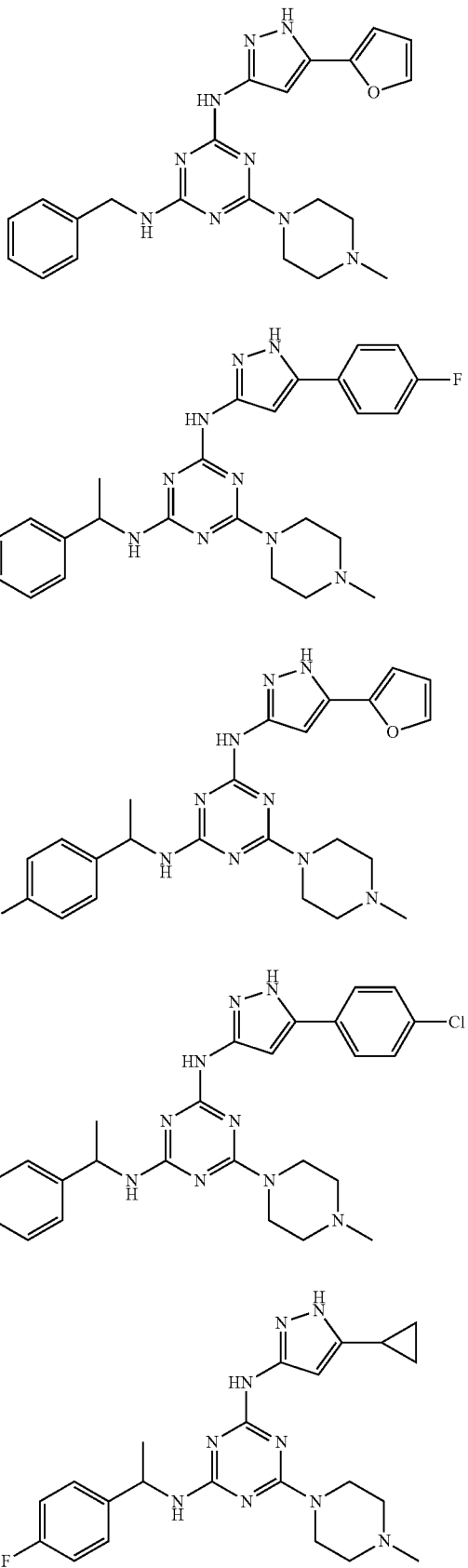

-continued
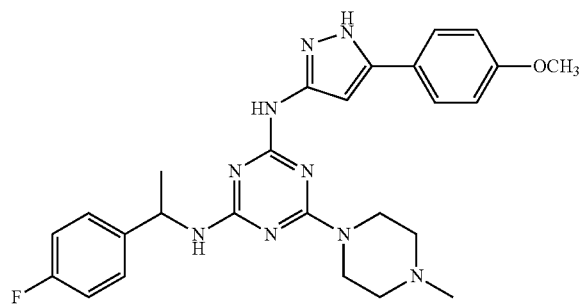
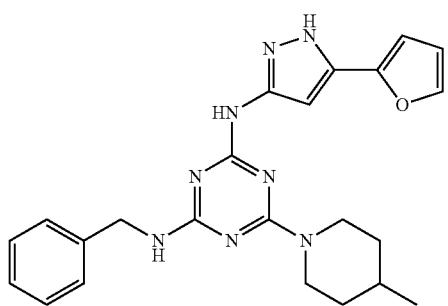
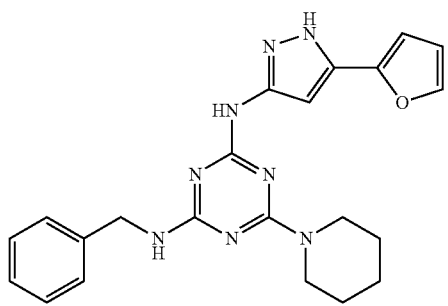
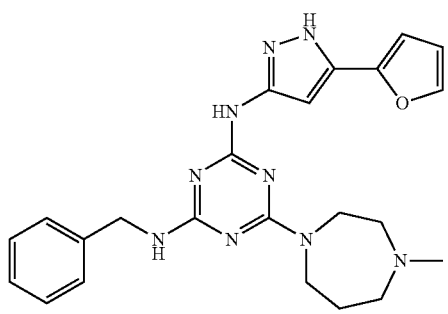
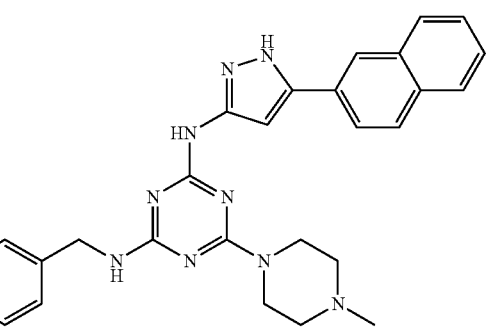
-continued
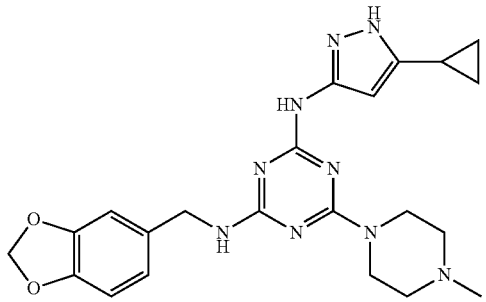
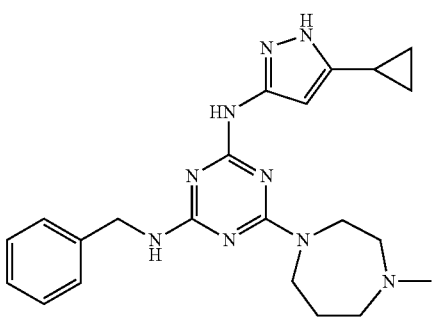
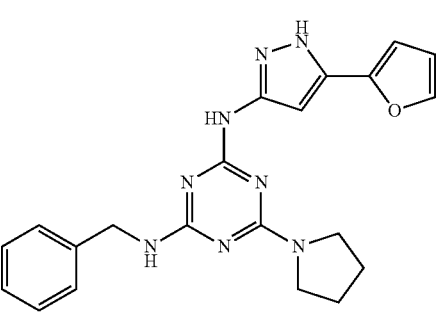
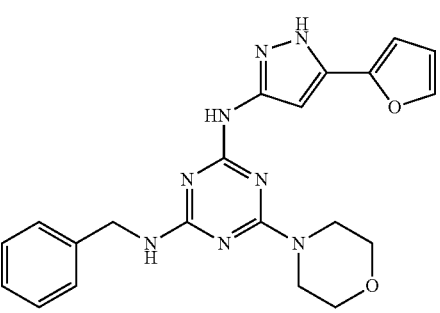
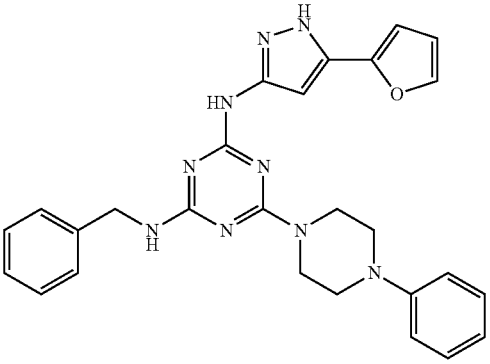

67
-continued
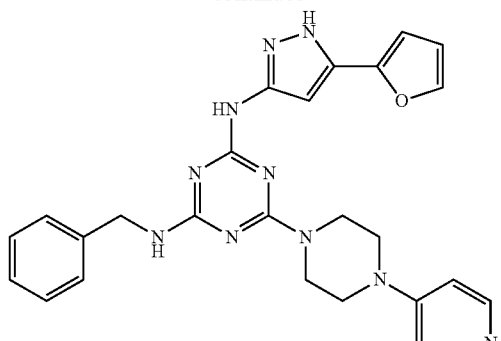
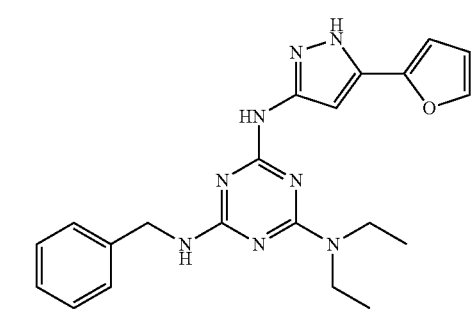
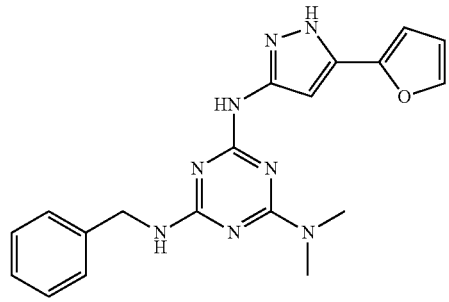
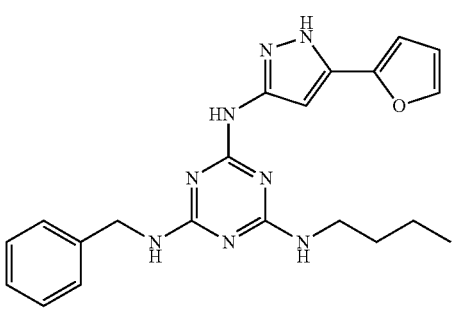
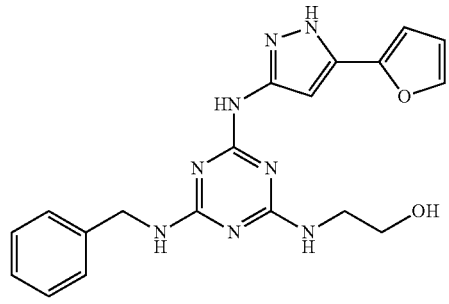
68
-continued
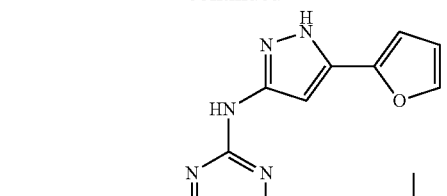
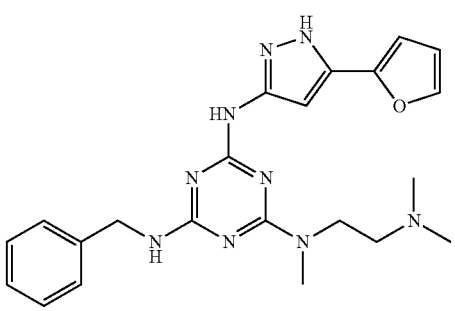
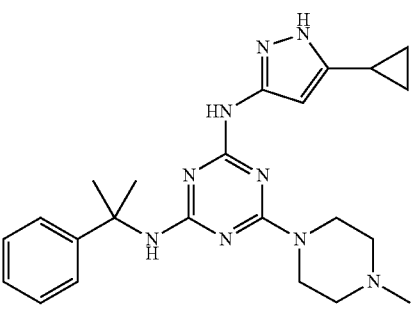
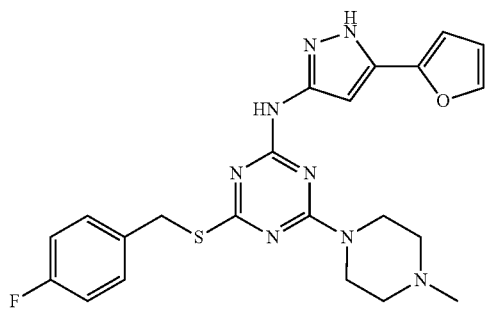
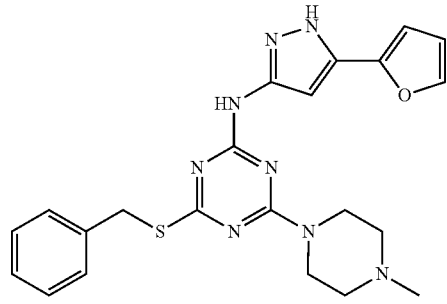

-continued
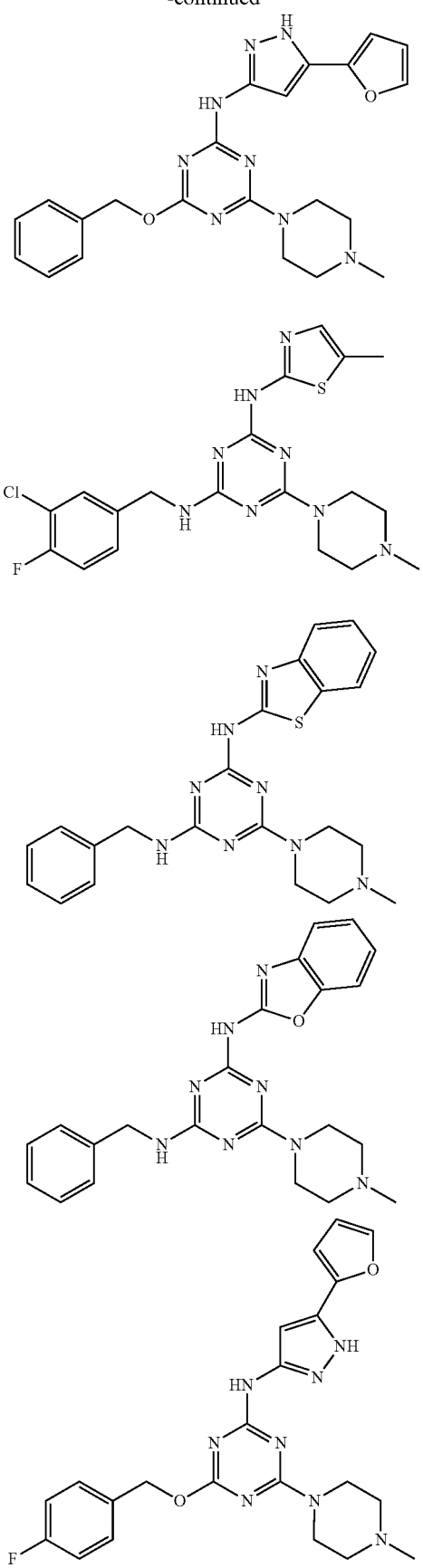
-continued
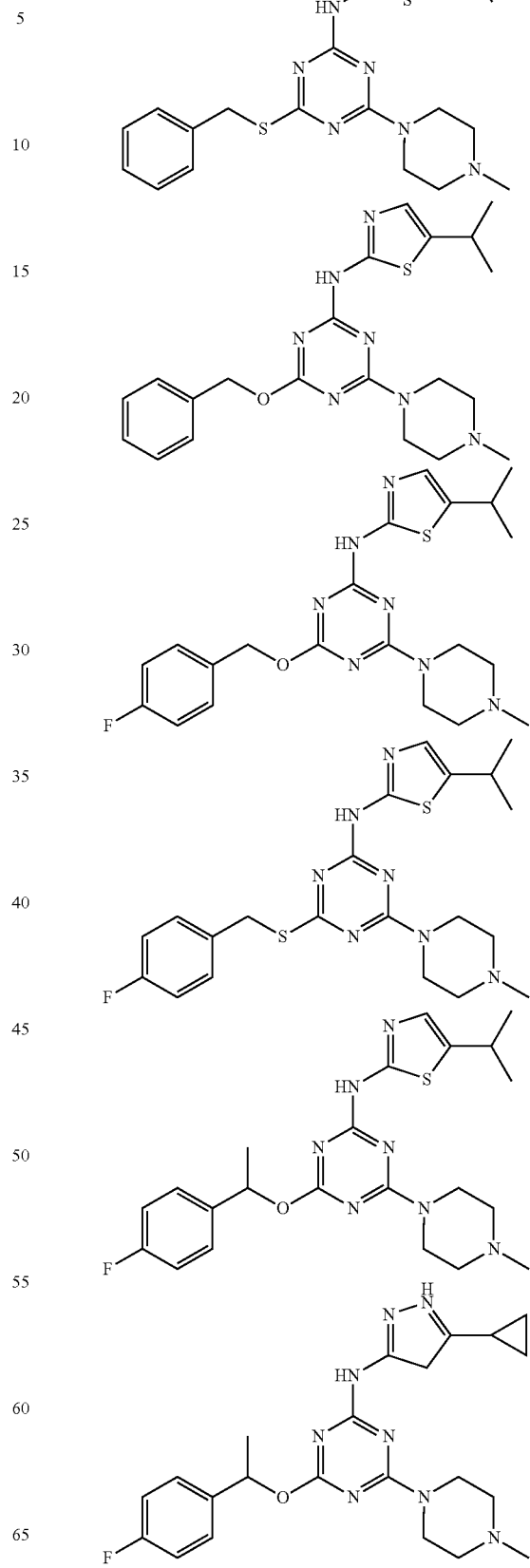

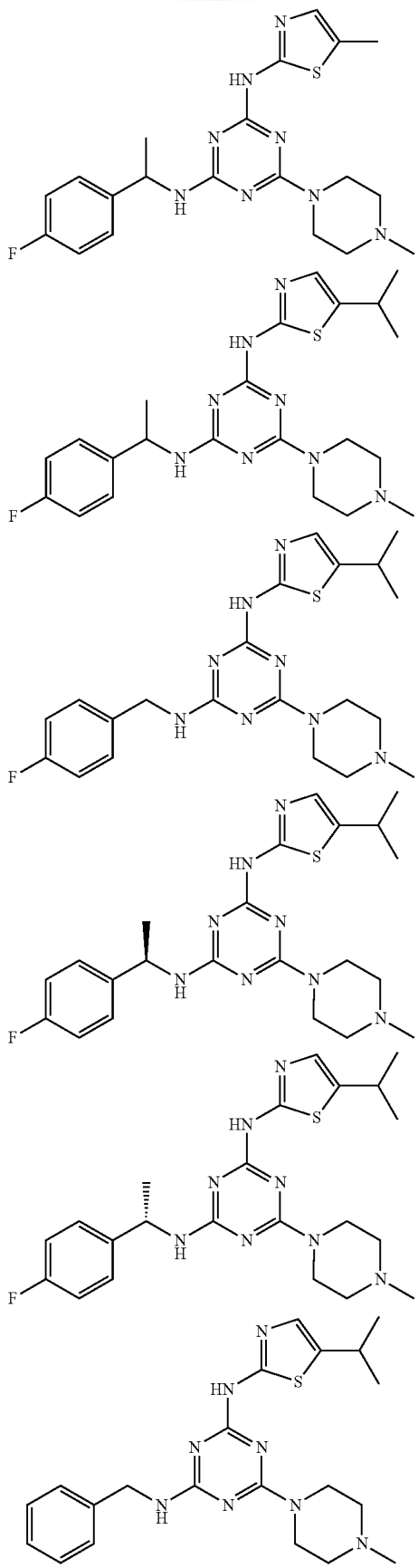

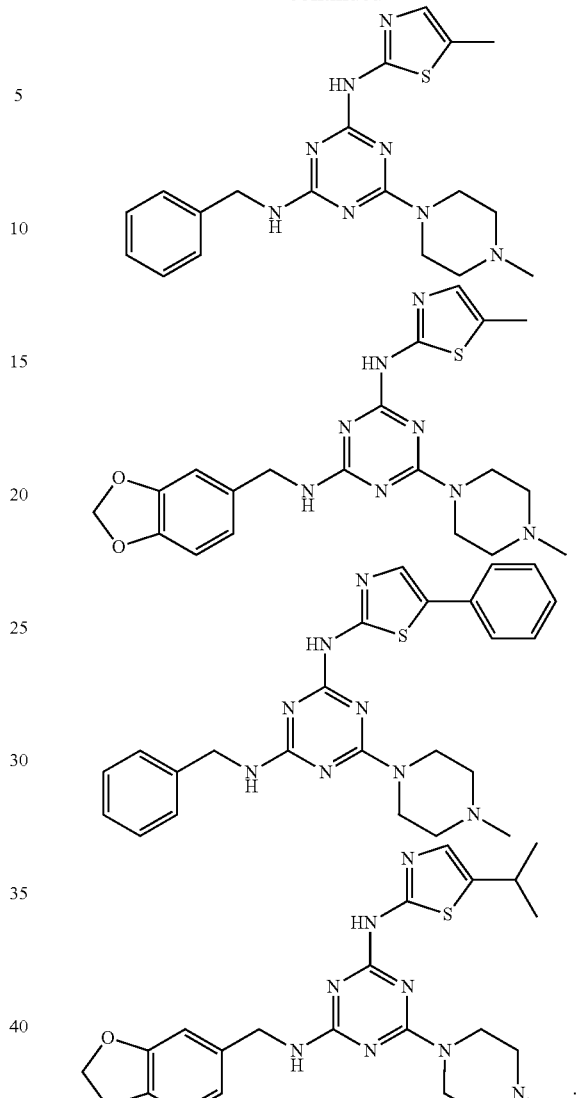

6. A compound as shown in Formula (A):

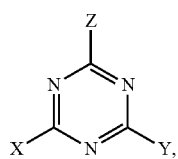

(A)

or a pharmaceutically acceptable salt thereof, wherein:
Y is selected from $C_1$-$C_6$ alkyl, $C_2$-$C_6$ alkenyl, $C_2$-$C_6$ alkynyl, —$NR^4R^5$, and -Q-$R^3$;
Q is heterocycloalkyl, which is optionally substituted with $C_1$-$C_4$ alkyl or oxo;
$R^3$ is selected from H, $C_1$-$C_6$ alkyl, $C_2$-$C_6$ alkenyl, $C_2$-$C_6$ alkynyl, aryl, and heteroaryl;
$R^4$ and $R^5$ are each independently selected from H, and $C_1$-$C_6$ alkyl;
X is —K—C($R^4$)($R^5$)—$Ar^1$—$R^1$;
K is selected from $NR^4$, S, and O;
$Ar^1$ is selected from aryl and heteroaryl, each of which is optionally substituted with halo, hydroxy, $C_1$-$C_6$ alkyl, $C_1$-$C_6$ haloalkyl, and $C_1$-$C_6$ alkoxy;

$R^1$ is one or more substituents independently selected from H, halo, —OR, $C_1$-$C_6$ alkyl, and $C_1$-$C_6$ haloalkyl;

Z is —NH—$Ar^2$—$R^2$;

$Ar^2$ is heteroaryl including at least one nitrogen, which heteroaryl is optionally substituted with halo, hydroxy, $C_1$-$C_6$ alkyl, $C_1$-$C_6$ haloalkyl, and $C_1$-$C_6$ alkoxy;

$R^2$ is one or more substituents independently selected from halo, hydroxy, $C_1$-$C_6$ alkyl, aryl, heteroaryl, $C_2$-$C_6$ alkenyl, and $C_2$-$C_6$ alkynyl, each of which is optionally substituted with halo, hydroxy, $C_1$-$C_6$ alkyl, $C_1$-$C_6$ haloalkyl, and $C_1$-$C_6$ alkoxy.

7. A process for making a compound of claim 6 or its pharmaceutically acceptable salts, hydrates, solvates, and individual diastereomers thereof.

8. A pharmaceutical composition comprising at least one compound of claim 6 or its pharmaceutically acceptable salts, hydrates, solvates, and individual diastereomers thereof, and a pharmaceutically acceptable carrier.

9. A compound as shown in Formula (A):

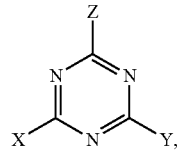

(A)

or a pharmaceutically acceptable salt thereof, wherein:

Y is -Q-$R^3$;

Q is piperazinyl;

$R^4$ and $R^5$ are each independently selected from H, and $C_1$-$C_6$ alkyl;

X is —K—C($R^4$)($R^5$)—$Ar^1$—$R^1$;

K is selected from $NR^4$, S, and O;

$Ar^1$ is selected from phenyl, and benzodioxolyl;

$R^1$ is selected from H, halo, —$OR^4$, and $C_1$-$C_6$ alkyl;

Z is —NH—$Ar^2$—$R^2$;

$Ar^2$ is selected from thiazolyl and pyrazolyl;

$R^2$ is one or more substituents independently selected from halo, hydroxy, $C_1$-$C_6$ alkyl, phenyl, furanyl, $C_2$-$C_6$ alkenyl, and $C_2$-$C_6$ alkynyl.

10. A process for making a compound of claim 9 or its pharmaceutically acceptable salts, hydrates, solvates, and individual diastereomers thereof.

11. A pharmaceutical composition comprising at least one compound of claim 9 or its pharmaceutically acceptable salts, hydrates, solvates, and individual diastereomers thereof, and a pharmaceutically acceptable carrier.

* * * * *